US009439599B2

(12) United States Patent
Thompson et al.

(10) Patent No.: US 9,439,599 B2
(45) Date of Patent: Sep. 13, 2016

(54) WEARABLE PERSONAL BODY ASSOCIATED DEVICE WITH VARIOUS PHYSICAL CONFIGURATIONS

(75) Inventors: Todd Thompson, San Jose, CA (US); Olivier Colliou, Los Gatos, CA (US); Robert Duck, San Francisco, CA (US); Yashar Behzadi, Anaheim, CA (US)

(73) Assignee: Proteus Digital Health, Inc., Redwood City, CA (US)

(*) Notice: Subject to any disclaimer, the term of this patent is extended or adjusted under 35 U.S.C. 154(b) by 0 days.

(21) Appl. No.: 14/004,399

(22) PCT Filed: Mar. 8, 2012

(86) PCT No.: PCT/US2012/028343
§ 371 (c)(1),
(2), (4) Date: Jan. 23, 2014

(87) PCT Pub. No.: WO2012/125425
PCT Pub. Date: Sep. 20, 2012

(65) Prior Publication Data
US 2014/0206976 A1    Jul. 24, 2014

Related U.S. Application Data

(60) Provisional application No. 61/452,042, filed on Mar. 11, 2011.

(51) Int. Cl.
*A61B 5/00*    (2006.01)
*A61B 5/0408*    (2006.01)
(Continued)

(52) U.S. Cl.
CPC ............ *A61B 5/6833* (2013.01); *A61B 5/0006* (2013.01); *A61B 5/0022* (2013.01);
(Continued)

(58) Field of Classification Search
CPC ............. A61B 5/0002; A61B 5/0024; A61B 5/02438; A61B 5/0408; A61B 5/04087; A61B 5/0492; A61B 5/6801; A61B 5/6832; A61B 5/6833; A61B 5/6844; A61B 2560/0412; A61B 2560/0468; A61B 2562/16; A61B 2562/164; A61B 2562/166; A61B 2562/182; A61B 5/002; A61B 5/061; A61B 5/0638
USPC ................ 600/392, 393, 382, 384, 301, 509
See application file for complete search history.

(56) References Cited

U.S. PATENT DOCUMENTS 3,340,866 A    9/1967 Noller
3,607,788 A    9/1971 Adolph
(Continued)

FOREIGN PATENT DOCUMENTS

CN    1588649    3/2005
CN    1991868    7/2007
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Lee S Cohen
*Assistant Examiner* — Erin M Cardinal
(74) *Attorney, Agent, or Firm* — K&L Gates LLP

(57) ABSTRACT

A body associated device comprises a housing, an adhesive layer configured to be applied to a body of a living subject, and at least one standoff located between the housing and the adhesive layer. An electronic module may be located within the housing of the body associated device. A personal communication system comprises a body associated device including an electronic module and further comprises a feedback portion coupled to the housing and to the electronic module. The feedback portion is configured to communicate information between the living subject and the body associated device. An external local node is operative to provide at least one of transmit communications to and receive communications from the body associated device.

17 Claims, 16 Drawing Sheets

(51) Int. Cl.

| | |
|---|---|
| *H04B 13/00* | (2006.01) |
| *A61B 5/04* | (2006.01) |
| *A61B 5/01* | (2006.01) |
| *A61B 5/021* | (2006.01) |
| *A61B 5/024* | (2006.01) |
| *A61B 5/042* | (2006.01) |
| *A61B 5/0476* | (2006.01) |
| *A61B 5/0488* | (2006.01) |
| *A61B 5/08* | (2006.01) |
| *A61B 5/11* | (2006.01) |
| *A61B 5/145* | (2006.01) |

(52) U.S. Cl.
CPC .......... *A61B5/0024* (2013.01); *A61B 5/0408* (2013.01); *A61B 5/04087* (2013.01); *H04B 13/005* (2013.01); *A61B 5/01* (2013.01); *A61B 5/021* (2013.01); *A61B 5/02405* (2013.01); *A61B 5/042* (2013.01); *A61B 5/0476* (2013.01); *A61B 5/0488* (2013.01); *A61B 5/0809* (2013.01); *A61B 5/1116* (2013.01); *A61B 5/1118* (2013.01); *A61B 5/145* (2013.01); *A61B 2560/0412* (2013.01); *A61B 2562/0219* (2013.01)

(56) References Cited

U.S. PATENT DOCUMENTS

| | | | |
|---|---|---|---|
| 3,642,008 A | | 2/1972 | Bolduc |
| 3,679,480 A | | 7/1972 | Brown et al. |
| 3,682,160 A | | 8/1972 | Murata |
| 3,719,183 A | | 3/1973 | Schwartz |
| 3,828,766 A | | 8/1974 | Krasnow |
| 3,837,339 A | | 9/1974 | Aisenberg et al. |
| 3,989,050 A | | 11/1976 | Buchalter |
| 4,067,014 A | | 1/1978 | Wheeler et al. |
| 4,077,397 A | | 3/1978 | Ellis |
| 4,077,398 A | | 3/1978 | Ellis |
| 4,082,087 A | | 4/1978 | Howson |
| 4,090,752 A | | 5/1978 | Long |
| 4,106,348 A | | 8/1978 | Auphan |
| 4,121,573 A | * | 10/1978 | Crovella et al. ............ 600/382 |
| 4,129,125 A | | 12/1978 | Lester |
| 4,166,453 A | | 9/1979 | McClelland |
| 4,185,172 A | | 1/1980 | Melindo et al. |
| 4,239,046 A | | 12/1980 | Ong |
| 4,269,189 A | | 5/1981 | Abraham |
| 4,331,654 A | | 5/1982 | Morris |
| 4,333,150 A | | 6/1982 | Matty et al. |
| 4,345,588 A | | 8/1982 | Widder et al. |
| 4,418,697 A | | 12/1983 | Tama |
| 4,425,117 A | | 1/1984 | Hugemann |
| 4,494,950 A | | 1/1985 | Fischell |
| 4,513,385 A | | 4/1985 | Muri |
| 4,559,950 A | | 12/1985 | Vaughan |
| 4,578,061 A | | 3/1986 | Lemelson |
| 4,635,641 A | | 1/1987 | Hoffman |
| 4,654,165 A | | 3/1987 | Eisenber |
| 4,669,479 A | | 6/1987 | Dunseath |
| 4,725,997 A | | 2/1988 | Urquhart et al. |
| 4,749,575 A | | 6/1988 | Rotman et al. |
| 4,763,659 A | | 8/1988 | Dunseath |
| 4,784,162 A | | 11/1988 | Ricks |
| 4,793,825 A | | 12/1988 | Benjamin et al. |
| 4,809,705 A | * | 3/1989 | Ascher ............ 600/523 |
| 4,844,076 A | | 7/1989 | Lesho |
| 4,858,617 A | * | 8/1989 | Sanders ............ 600/509 |
| 4,896,261 A | | 1/1990 | Nolan |
| 4,975,230 A | | 12/1990 | Pinkhasov |
| 4,987,897 A | * | 1/1991 | Funke ............ 607/32 |
| 5,016,634 A | | 5/1991 | Vock et al. |
| 5,079,006 A | | 1/1992 | Urguhart |
| 5,113,859 A | * | 5/1992 | Funke ............ 607/4 |
| 5,167,626 A | | 12/1992 | Casper |
| 5,176,626 A | | 1/1993 | Soehendra |
| 5,232,383 A | | 8/1993 | Barnick |
| 5,261,402 A | | 11/1993 | DiSabito |
| 5,263,481 A | | 11/1993 | Axelgaard et al. |
| 5,281,287 A | | 1/1994 | Lloyd |
| 5,283,136 A | | 2/1994 | Peled et al. |
| 5,318,557 A | | 6/1994 | Gross |
| 5,394,882 A | | 3/1995 | Mawhinney |
| 5,458,141 A | | 10/1995 | Neil et al. |
| 5,485,841 A | | 1/1996 | Watkin et al. |
| 5,511,548 A | | 4/1996 | Riazzi et al. |
| 5,551,020 A | | 8/1996 | Flax et al. |
| 5,596,302 A | | 1/1997 | Mastrocola et al. |
| D377,983 S | * | 2/1997 | Sabri et al. ............ D24/167 |
| 5,634,466 A | | 6/1997 | Gruner |
| 5,634,468 A | | 6/1997 | Platt |
| 5,645,063 A | | 7/1997 | Straka et al. |
| 5,720,771 A | | 2/1998 | Snell |
| 5,724,432 A | | 3/1998 | Bouvet et al. |
| 5,740,811 A | | 4/1998 | Hedberg |
| 5,792,048 A | | 8/1998 | Schaefer |
| 5,802,467 A | | 9/1998 | Salazar |
| 5,833,716 A | | 11/1998 | Bar-Or |
| 5,845,265 A | | 12/1998 | Woolston |
| 5,862,803 A | | 1/1999 | Besson |
| 5,862,808 A | | 1/1999 | Albarello |
| 5,868,136 A | | 2/1999 | Fox |
| 5,921,925 A | | 7/1999 | Cartmell et al. |
| 5,925,030 A | | 7/1999 | Gross et al. |
| 5,925,066 A | | 7/1999 | Kroll et al. |
| 5,957,854 A | | 9/1999 | Besson et al. |
| 5,974,124 A | | 10/1999 | Schlueter, Jr. et al. |
| 5,981,166 A | | 11/1999 | Mandecki |
| 5,999,846 A | | 12/1999 | Pardey et al. |
| 6,023,631 A | | 2/2000 | Cartmell et al. |
| 6,038,464 A | | 3/2000 | Axelgaard et al. |
| 6,042,710 A | | 3/2000 | Dubrow |
| 6,047,203 A | | 4/2000 | Sackner |
| 6,081,734 A | | 6/2000 | Batz |
| 6,095,985 A | | 8/2000 | Raymond et al. |
| 6,115,636 A | * | 9/2000 | Ryan ............ 607/60 |
| 6,117,077 A | * | 9/2000 | Del Mar et al. ............ 600/301 |
| 6,122,351 A | | 9/2000 | Schlueter, Jr. et al. |
| 6,141,592 A | | 10/2000 | Pauly |
| 6,200,265 B1 | * | 3/2001 | Walsh et al. ............ 600/300 |
| 6,200,625 B1 | | 3/2001 | Beckett |
| 6,204,764 B1 | | 3/2001 | Maloney |
| 6,206,702 B1 | | 3/2001 | Hayden et al. |
| 6,217,744 B1 | | 4/2001 | Crosby |
| 6,231,593 B1 | | 5/2001 | Meserol |
| 6,238,338 B1 | * | 5/2001 | DeLuca et al. ............ 600/300 |
| 6,245,057 B1 | | 6/2001 | Sieben et al. |
| 6,275,476 B1 | | 8/2001 | Wood |
| 6,285,897 B1 | | 9/2001 | Kilcoyne et al. |
| 6,287,252 B1 | | 9/2001 | Lugo |
| 6,289,238 B1 | | 9/2001 | Besson et al. |
| 6,301,298 B1 | | 10/2001 | Kuntz et al. |
| 6,315,719 B1 | | 11/2001 | Rode et al. |
| 6,317,714 B1 | | 11/2001 | Del Castillo |
| 6,358,202 B1 | | 3/2002 | Arent |
| 6,364,834 B1 | | 4/2002 | Reuss |
| 6,366,206 B1 | | 4/2002 | Ishikawa et al. |
| 6,371,927 B1 | | 4/2002 | Brune |
| 6,374,670 B1 | | 4/2002 | Spelman |
| 6,380,858 B1 | | 4/2002 | Yarin et al. |
| 6,394,953 B1 | * | 5/2002 | Devlin et al. ............ 600/383 |
| 6,394,997 B1 | | 5/2002 | Lemelson |
| 6,409,674 B1 | | 6/2002 | Brockway et al. |
| 6,426,863 B1 | | 7/2002 | Munshi |
| 6,432,292 B1 | | 8/2002 | Pinto et al. |
| 6,440,069 B1 | | 8/2002 | Raymond et al. |
| 6,441,747 B1 | | 8/2002 | Khair |
| 6,477,424 B1 | | 11/2002 | Thompson et al. |
| 6,482,156 B2 | | 11/2002 | Lliff |
| 6,494,829 B1 | | 12/2002 | New et al. |
| 6,496,705 B1 | | 12/2002 | Ng et al. |
| 6,526,315 B1 | | 2/2003 | Inagawa |
| 6,544,174 B2 | | 4/2003 | West |
| 6,564,079 B1 | | 5/2003 | Cory |

(56) References Cited

U.S. PATENT DOCUMENTS

| | | |
|---|---|---|
| 6,577,893 B1 | 6/2003 | Besson et al. |
| 6,579,231 B1 | 6/2003 | Phipps |
| 6,605,038 B1 | 8/2003 | Teller et al. |
| 6,605,046 B1 * | 8/2003 | Del Mar ............... 600/507 |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,856,832 B1 * | 2/2005 | Matsumura et al. ......... 600/523 |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,956,917 B2 | 10/2005 | Lenosky |
| 6,957,107 B2 | 10/2005 | Rogers et al. |
| 6,959,929 B2 | 11/2005 | Pugnet et al. |
| 6,961,601 B2 | 11/2005 | Mathews et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,046,649 B2 | 5/2006 | Awater et al. |
| 7,076,437 B1 | 7/2006 | Levy |
| 7,116,252 B2 | 10/2006 | Teraguchi |
| 7,118,531 B2 | 10/2006 | Krill |
| 7,127,300 B2 | 10/2006 | Mazar et al. |
| 7,139,332 B2 | 11/2006 | Yu et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,154,916 B2 | 12/2006 | Soloff |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,105 B2 | 7/2008 | Schmidt et al. |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,512,448 B2 | 3/2009 | Malick |
| 7,515,043 B2 | 4/2009 | Welch |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,599,003 B2 | 10/2009 | Suzuki et al. |
| 7,616,111 B2 | 11/2009 | Covannon |
| 7,616,710 B2 | 11/2009 | Kim et al. |
| 7,617,001 B2 | 11/2009 | Penner et al. |
| 7,626,387 B2 | 12/2009 | Adachi |
| 7,640,802 B2 | 1/2010 | King et al. |
| 7,647,112 B2 | 1/2010 | Tracey |
| 7,647,185 B2 | 1/2010 | Tarassenko et al. |

(56) References Cited

U.S. PATENT DOCUMENTS

| | | |
|---|---|---|
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,688,204 B2 | 3/2010 | Yamanaka et al. |
| 7,689,437 B1 | 3/2010 | Teller et al. |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,782,991 B2 | 8/2010 | Sobchak et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| D639,437 S * | 6/2011 | Bishay et al. ............... D24/167 |
| 7,983,189 B2 | 7/2011 | Bugenhagen |
| 8,036,748 B2 | 10/2011 | Zdeblick et al. |
| 8,073,707 B2 | 12/2011 | Teller et al. |
| 8,083,128 B2 | 12/2011 | Dembo et al. |
| 8,114,021 B2 | 2/2012 | Robertson et al. |
| 8,123,576 B2 | 2/2012 | Kim |
| 8,140,143 B2 | 3/2012 | Picard et al. |
| 8,170,515 B2 | 5/2012 | Le Reverend et al. |
| 8,180,425 B2 | 5/2012 | Selvitelli et al. |
| 8,184,854 B2 | 5/2012 | Bartsch |
| 8,193,821 B2 | 6/2012 | Mueller |
| 8,200,320 B2 | 6/2012 | Kovacs |
| 8,214,007 B2 | 7/2012 | Baker et al. |
| 8,238,998 B2 | 8/2012 | Park |
| 8,249,686 B2 | 8/2012 | Libbus et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 8,404,275 B2 | 3/2013 | Habboushe |
| 8,440,274 B2 * | 5/2013 | Wang ............................ 428/34.1 |
| 8,471,960 B2 | 6/2013 | Lin et al. |
| 8,514,979 B2 | 8/2013 | Laporte |
| 8,604,674 B2 | 12/2013 | Fujimoto |
| 8,615,290 B2 | 12/2013 | Lin et al. |
| 8,620,402 B2 | 12/2013 | Parker, III et al. |
| 8,754,799 B2 | 6/2014 | Coln et al. |
| 8,773,258 B2 | 7/2014 | Vosch et al. |
| 8,836,513 B2 | 9/2014 | Hafezi et al. |
| 8,932,221 B2 | 1/2015 | Colliou et al. |
| 8,945,005 B2 | 2/2015 | Hafezi et al. |
| 9,014,779 B2 | 4/2015 | Zdeblick et al. |
| 9,149,577 B2 | 10/2015 | Robertson et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdinski |
| 2001/0056262 A1 * | 12/2001 | Cabiri et al. ................. 604/180 |
| 2002/0002326 A1 | 1/2002 | Causey et al. |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0169696 A1 | 11/2002 | Zara |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0091121 A1 | 5/2003 | Kenmochi |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0162469 A1 * | 8/2004 | Imran .......................... 600/310 |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0010338 A1 | 1/2005 | Kraeling et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |

(56) References Cited

U.S. PATENT DOCUMENTS

| | | |
|---|---|---|
| 2005/0137480 A1 | 6/2005 | Alt et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0136744 A1 | 6/2006 | Lange |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0265246 A1 | 11/2006 | Hoag |
| 2006/0270346 A1 | 11/2006 | Ibrahim |
| 2006/0277097 A1 | 12/2006 | Shafron et al. |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0069887 A1* | 3/2007 | Welch et al. ............ 340/539.12 |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0249946 A1* | 10/2007 | Kumar et al. ................ 600/515 |
| 2007/0255153 A1 | 11/2007 | Kumar |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0014866 A1 | 1/2008 | Lipowshi |
| 2008/0015421 A1 | 1/2008 | Penner |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0045843 A1 | 2/2008 | Tsuji et al. |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1* | 9/2008 | Gehman ............ A61B 5/0006 600/391 |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |

(56) References Cited

U.S. PATENT DOCUMENTS

| | | |
|---|---|---|
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076340 A1 | 3/2009 | Libbus et al. |
| 2009/0076343 A1 | 3/2009 | James |
| 2009/0076350 A1* | 3/2009 | Bly ............... A61B 5/0006 600/301 |
| 2009/0076397 A1 | 3/2009 | Libbus et al. |
| 2009/0082645 A1 | 3/2009 | Hafezi et al. |
| 2009/0088618 A1 | 4/2009 | Arneson |
| 2009/0099435 A1 | 4/2009 | Say et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0010330 A1 | 1/2010 | Rankers |
| 2010/0033324 A1 | 2/2010 | Shimizu et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0049263 A1 | 2/2010 | Reeve |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0081913 A1 | 4/2010 | Cross et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0160762 A1* | 6/2010 | McLaughlin et al. ........ 600/372 |
| 2010/0168659 A1 | 7/2010 | Say et al. |

(56) References Cited

U.S. PATENT DOCUMENTS

| | | | |
|---|---|---|---|
| 2010/0179398 A1 | 7/2010 | Say et al. | |
| 2010/0185055 A1 | 7/2010 | Robertson | |
| 2010/0191073 A1 | 7/2010 | Tarassenko et al. | |
| 2010/0210299 A1 | 8/2010 | Gorbachov | |
| 2010/0222652 A1 | 9/2010 | Cho | |
| 2010/0228113 A1* | 9/2010 | Solosko et al. | 600/382 |
| 2010/0234706 A1 | 9/2010 | Gilland | |
| 2010/0234715 A1 | 9/2010 | Shin | |
| 2010/0234914 A1 | 9/2010 | Shen | |
| 2010/0245091 A1 | 9/2010 | Singh | |
| 2010/0249881 A1 | 9/2010 | Corndorf | |
| 2010/0256461 A1 | 10/2010 | Mohamedali | |
| 2010/0259543 A1 | 10/2010 | Tarassenko et al. | |
| 2010/0268048 A1 | 10/2010 | Say et al. | |
| 2010/0268049 A1 | 10/2010 | Say et al. | |
| 2010/0268050 A1 | 10/2010 | Say et al. | |
| 2010/0274111 A1 | 10/2010 | Say et al. | |
| 2010/0280345 A1 | 11/2010 | Say et al. | |
| 2010/0280346 A1 | 11/2010 | Say et al. | |
| 2010/0298650 A1 | 11/2010 | Moon et al. | |
| 2010/0298730 A1 | 11/2010 | Tarassenko et al. | |
| 2010/0311482 A1 | 12/2010 | Lange | |
| 2010/0312188 A1* | 12/2010 | Robertson et al. | 604/156 |
| 2010/0312580 A1 | 12/2010 | Tarassenko et al. | |
| 2011/0004079 A1 | 1/2011 | Al-Ali et al. | |
| 2011/0040203 A1 | 2/2011 | Savage et al. | |
| 2011/0065983 A1 | 3/2011 | Hafezi et al. | |
| 2011/0081860 A1 | 4/2011 | Brown et al. | |
| 2011/0124983 A1 | 5/2011 | Kroll et al. | |
| 2011/0144470 A1 | 6/2011 | Mazar et al. | |
| 2011/0166937 A1 | 7/2011 | Bangera et al. | |
| 2011/0237924 A1 | 9/2011 | McGusty et al. | |
| 2011/0279963 A1* | 11/2011 | Kumar et al. | 361/679.31 |
| 2012/0016231 A1 | 1/2012 | Westmoreland | |
| 2012/0029307 A1* | 2/2012 | Paquet et al. | 600/301 |
| 2012/0029309 A1 | 2/2012 | Paquet et al. | |
| 2012/0071743 A1* | 3/2012 | Todorov | G06F 19/3481 600/372 |
| 2012/0089000 A1* | 4/2012 | Bishay et al. | 600/391 |
| 2012/0101396 A1 | 4/2012 | Solosko et al. | |
| 2012/0197144 A1 | 8/2012 | Christ et al. | |
| 2012/0299723 A1 | 11/2012 | Hafezi et al. | |
| 2012/0310070 A1 | 12/2012 | Kumar et al. | |
| 2012/0316413 A1 | 12/2012 | Liu et al. | |
| 2013/0030259 A1 | 1/2013 | Thomsen et al. | |
| 2013/0057385 A1 | 3/2013 | Murakami et al. | |
| 2013/0060115 A1 | 3/2013 | Gehman et al. | |
| 2014/0300490 A1 | 10/2014 | Kotz et al. | |
| 2015/0080677 A1 | 3/2015 | Thompson et al. | |
| 2015/0080678 A1 | 3/2015 | Frank et al. | |
| 2015/0080679 A1 | 3/2015 | Frank et al. | |
| 2015/0080680 A1 | 3/2015 | Zdeblick et al. | |
| 2015/0080681 A1 | 3/2015 | Hafezi et al. | |
| 2015/0127737 A1 | 5/2015 | Thompson et al. | |
| 2015/0127738 A1 | 5/2015 | Thompson et al. | |
| 2015/0131764 A1 | 5/2015 | Kushner et al. | |
| 2015/0182170 A1 | 7/2015 | Zdeblick et al. | |
| 2015/0248833 A1 | 9/2015 | Arne et al. | |

FOREIGN PATENT DOCUMENTS

| | | |
|---|---|---|
| CN | 101005470 | 7/2007 |
| CN | 101032396 | 9/2007 |
| CN | 201076456 | 6/2008 |
| DE | 10313005 | 10/2004 |
| EP | 1246356 | 10/2002 |
| EP | 1789128 | 5/2007 |
| EP | 2063535 | 5/2009 |
| EP | 2143369 | 1/2010 |
| JP | 61072712 | 4/1986 |
| JP | 05-228128 | 9/1993 |
| JP | 10-14898 | 1/1998 |
| JP | 2000-506410 | 5/2000 |
| JP | 2002-224053 | 8/2002 |
| JP | 2002282219 | 10/2002 |
| JP | 2002291684 | 10/2002 |
| JP | 2003050867 | 2/2003 |
| JP | 2004-7187 | 1/2004 |
| JP | 2004313242 | 11/2004 |
| JP | 2005-073886 | 3/2005 |
| JP | 2005-304880 | 4/2005 |
| JP | 2005137683 | 6/2005 |
| JP | 2005-532841 | 11/2005 |
| JP | 2005-532849 | 11/2005 |
| JP | 2006508752 | 3/2006 |
| JP | 2006509574 | 3/2006 |
| JP | 2006136405 | 6/2006 |
| JP | 2006-177699 | 7/2006 |
| JP | 2007167448 | 7/2007 |
| JP | 2007-313340 | 12/2007 |
| JP | 2008501415 | 1/2008 |
| JP | 2008086390 | 4/2008 |
| JP | 2008191110 | 8/2008 |
| JP | 2009528909 | 8/2009 |
| KR | 10-2009-0008786 | 1/2009 |
| KR | 927471 | 11/2009 |
| KR | 10-2012-09995 | 9/2012 |
| TW | 553735 | 9/2003 |
| TW | 200724094 | 7/2007 |
| WO | WO8802237 | 4/1988 |
| WO | WO9308734 | 5/1993 |
| WO | WO9319667 | 10/1993 |
| WO | WO9843537 | 10/1998 |
| WO | WO9959465 | 11/1999 |
| WO | WO0033246 | 6/2000 |
| WO | WO0100085 | 1/2001 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004066834 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005013503 | 2/2005 |
| WO | WO2005020023 | 3/2005 |
| WO | WO2005024687 | 3/2005 |
| WO | WO2005047837 | 5/2005 |
| WO | WO2005051166 | 6/2005 |
| WO | WO2005055448 | 6/2005 |
| WO | WO2005082436 | 9/2005 |
| WO | WO2005110238 | 11/2005 |
| WO | WO2006027586 | 3/2006 |
| WO | WO2006035351 | 4/2006 |
| WO | WO2006055892 | 5/2006 |
| WO | WO2006055956 | 5/2006 |
| WO | WO2006066566 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |

(56) References Cited

FOREIGN PATENT DOCUMENTS

| | | |
|---|---|---|
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127455 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008002239 | 1/2008 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080843 | 7/2010 |
| WO | WO2010105053 | 9/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2012104657 | 8/2012 |
| WO | WO2012158190 | 11/2012 |
| WO | WO2013012869 | 1/2013 |
| WO | WO2015042411 | 3/2015 |
| WO | WO2015044722 | 4/2015 |
| WO | WO2015112603 | 7/2015 |

OTHER PUBLICATIONS

Arshak et al., A Review and Adaptation of Methods of Object Tracking to Telemetry Capsules IC-Med (2007) vol. 1, No. 1, Issue 1, 12 pp.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Delvaux et al., "Capsule endoscopy: Technique and indications" Clinical Gastoenterology (2008) vol. 22, Issue 5, pp. 813-837.

Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Halthion Medical Technologies "Providing Ambulatory Medical Devices Which Monitor, Measure and Record" webpage. Online website: http://www.halthion.com/; downloaded May 30, 2012.

Heydari et al., "Analysis of the PLL jitter due to power/ground and substrate noise"; IEEE Transactions on Circuits and Systems (2004) 51(12): 2404-16.

Hoover et al., "Rx for health: Engineers design pill that signals it has been swallowed" University of Florida News (2010) 2pp.; http://news.ufl.edu/2010/03/31/antenna-pill-2/.

Hotz "The Really Smart Phone" The Wall Street Journal, What They Know (2011); 6 pp.; http://online.wsj.com/article/SB10001424052748704547604576263261679848814.html?mod=djemTECH_t.

ISFET—Ion Sensitive Field-Effect Transistor; Microsens S.A. pdf document. First in Office Action dated Jun. 13, 2011 for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Juvenile Diabetes Research Foundation International (JDRF), "Artificial Pancreas Project" (2010); http://www.artificialpancreasproject.com/; 3 pp.

Li, P-Y, et al. "An electrochemical intraocular drug delivery device", Sensors and Actuators A 143 (2008) p. 41-48.

Lifescan, "OneTouch UltraLink™" http://www.lifescan.com/products/meters/ultralink (2010) 2 pp.

MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

(56) References Cited

OTHER PUBLICATIONS

Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® Real-Time Revel™ System" (2010) http://www.medtronicdiabetes.com/products/index.html; 2 pp.
Medtronic, "Mini Med Paradigm® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/.
MiniMitter Co. Inc. "Actiheart" Traditional 510(k) Summary. Sep. 27, 2005.
Minimitter Co. Inc. Noninvasive technology to help your studies succeed. MiniMitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
MiniMitter Co. Inc. VitalSense Integrated Physiological Monitoring System. Product Description. (2005).
MiniMitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
"New 'smart pill' to track adherence" E-Health-Insider (2010) http://www.e-health-insider.com/news/5910/new_'smart_pill'_monitors_medicines.
NPL_AntennaBasics.pdf, Radio Antennae, http://www.erikdeman.de/html/sail018h.htm; (2008) 3pp.
Owano, N., "Study proposes smart sutures with sensors for wounds" phys.org. Aug. 2012. http://phys.org/news/2012-08-smart-sutures-sensors-wounds.html.
Park, "Medtronic to Buy MiniMed for $3.7 Billion" (2001) HomeCare; http://homecaremag.com/mag/medical_medtronic_buy_minimed/; 2 pp.
"RFID "pill" monitors marchers" RFID News (2008) http://www.rfidnews.org/2008/07/23/rfid-pill-monitors-marchers/.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.
"Smartlife awarded patent for knitted transducer" Innovation in Textiles News: http://www.innovationintextiles.com/articles/208.php; 2pp. (2009).
"The SmartPill Wireless Motility Capsule" SmartPill, The Measure of GI Health; (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Walkey, "MOSFET Structure and Processing"; 97.398* Physical Electronics Lecture 20; First in Office Action dated Jun. 13, 2011 for U.S. Appl. No. 12/238,345; 24 pp.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
Au-Yeung, K., et al., "A Networked System for Self-Management of Drug Therapy and Wellness", Wireless Health '10, Oct. 5-7, 2010, San Diego, 9 pages.

* cited by examiner

# WEARABLE PERSONAL BODY ASSOCIATED DEVICE WITH VARIOUS PHYSICAL CONFIGURATIONS

CROSS REFERENCE TO RELATED APPLICATIONS

This application is a 371 national stage filing of International Patent Application No. PCT/US2012/028343, entitled WEARABLE PERSONAL BODY ASSOCIATED DEVICE WITH VARIOUS PHYSICAL CONFIGURATIONS, filed Mar. 8, 2012, which application claims the benefit of U.S. Provisional Patent Application No. 61/452,042 entitled WEARABLE PERSONAL BODY ASSOCIATED DEVICE WITH VARIOUS PHYSICAL CONFIGURATIONS and filed on Mar. 11, 2011, which applications are herein entirely incorporated by reference.

INTRODUCTION

The present disclosure is related generally to various configurations of a body associated device such as a patch, wearable personal communication device, and the like. In particular, the present disclosure is related to various physical configurations of a wearable body associated device with structural features that enhance a living subject's experience and comfort when wearing the body associated device.

A broad industry with diverse product offerings is developing around body associated devices. Such devices include patches, personal monitors that sense physiologic parameters of a living subject and communicate such information to body-area network devices in communication with the personal monitor, personal communication devices, and the like. Body associated devices can monitor and record individual physiology, e.g., physical activity, heart rate, respiration, temperature, sleep, etc., of the living subject and communicate these parameters beyond the body of the living subject to other devices, e.g., mobile phones, computers, internet servers, etc. A challenge for such body associated devices is for an individual to wear or use such a device on a continuous basis—for example, to apply an adhesive bandage-based personal monitor to their skin for weeks, months and potentially years and accept the possibility of its inconveniences and limitations, such as (i) potential skin irritation, (ii) the burden of frequent application and removal, and (iii) a feeling of intrusiveness into the wearer's daily life.

Accordingly, there is a need for a wearable personal body associated device with physical characteristics that offer functional capabilities for which they are designed for as well as structural integrity and comfort for the living subject to wear and are easy to apply and remove from the body of the living subject.

SUMMARY

In one aspect, a body associated device comprises a housing, an adhesive layer configured to be applied to a body of a living subject, and at least one standoff located between the housing and the adhesive layer.

In another aspect, an electronic module may be located within the housing of the body associated device.

In yet another aspect, a personal communication system comprises a body associated device comprising an electronic module and further comprises a feedback portion coupled to the housing and coupled to the electronic module. The feedback portion is configured to communicate information between the living subject and the body associated device. An external local node is operative to provide at least one of transmit communications to and receive communications from the body associated device.

FIGURES

FIGS. 28A-D illustrate various standoffs having different continuous forms.

FIGS. 29A-D illustrate various standoffs having different broken forms.

Figure 30:
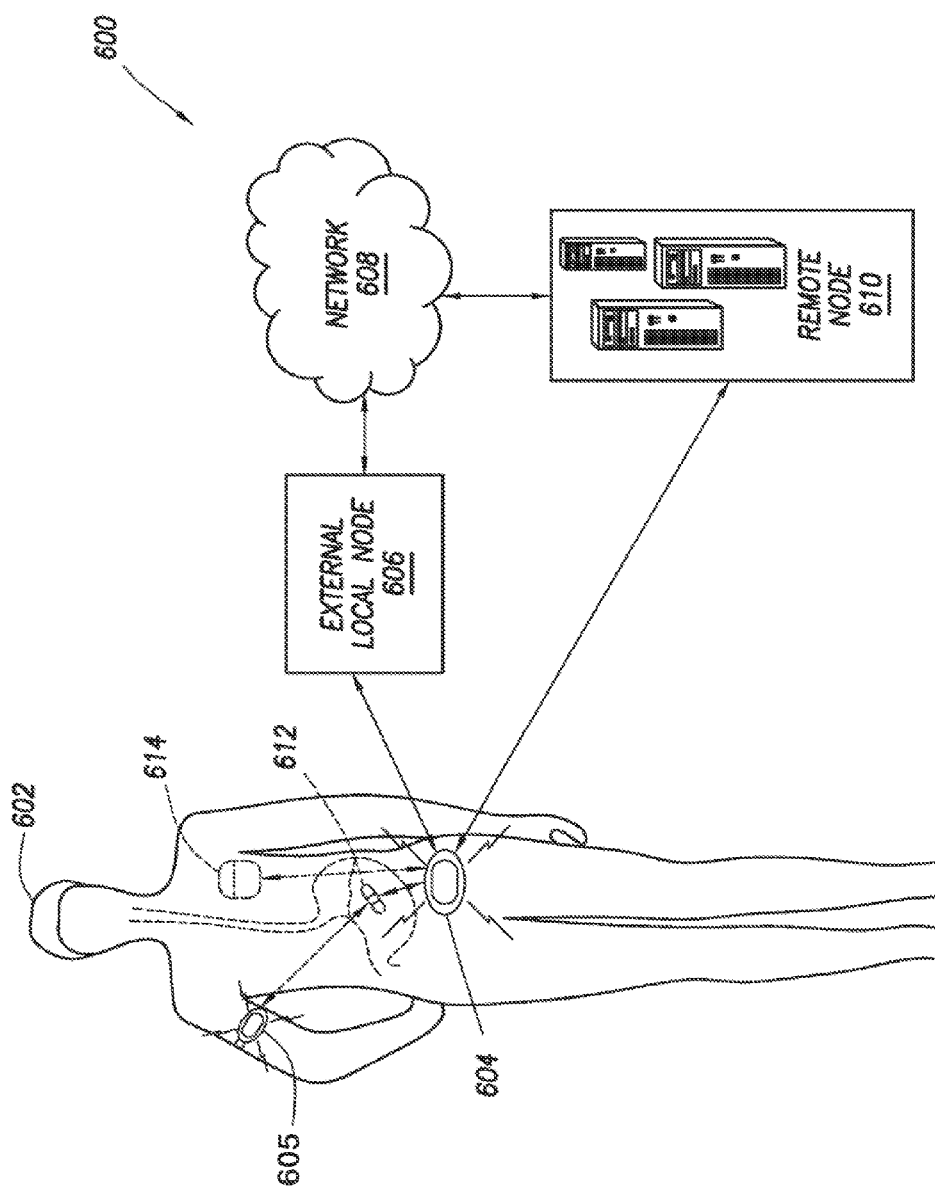

FIG. 30 illustrates one aspect of a personal communication system in which the body associated device described herein may be employed.

Figure 31:
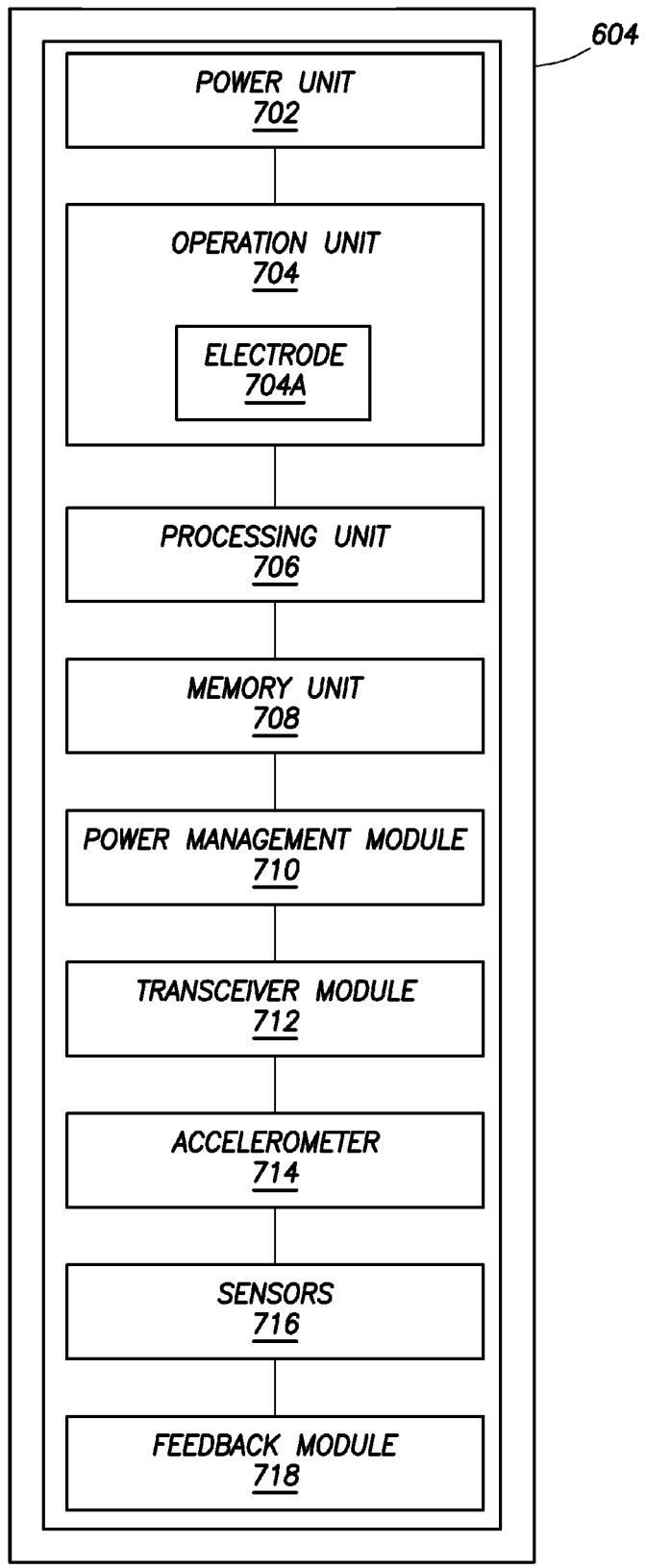

FIG. 31 is a block diagram of one aspect of a body associated device.

Figure 32:
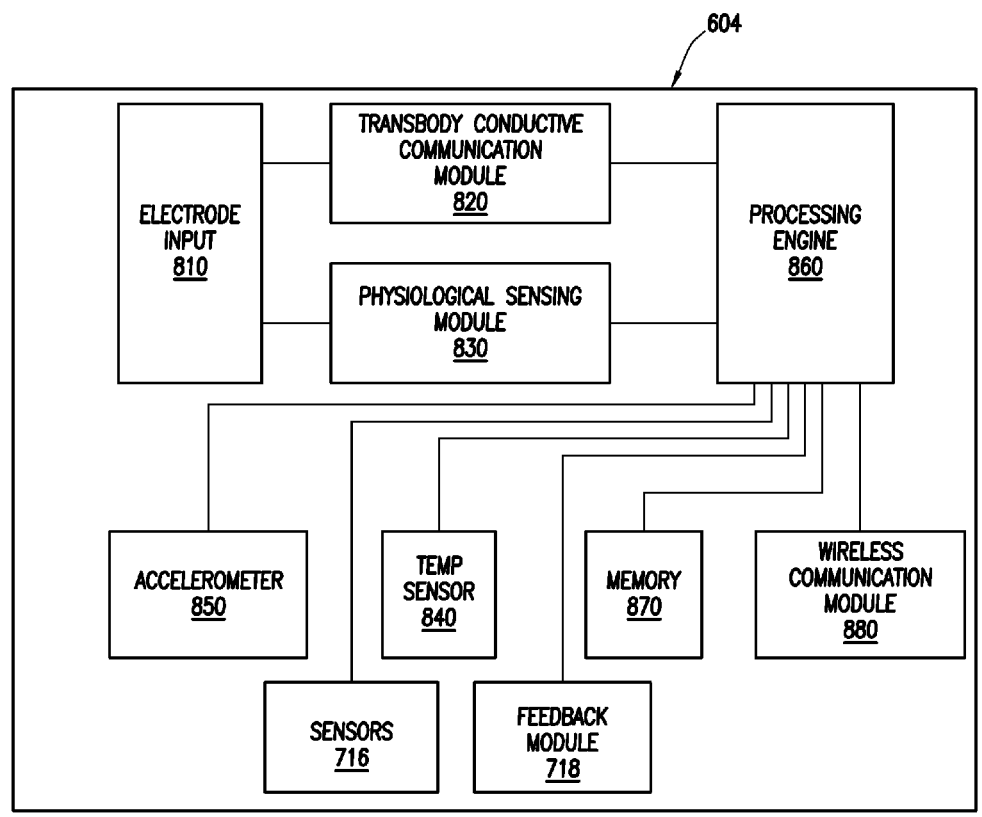

FIG. 32 is a block functional diagram of one aspect of an electronic circuit component of a body associated device.

Figure 33:
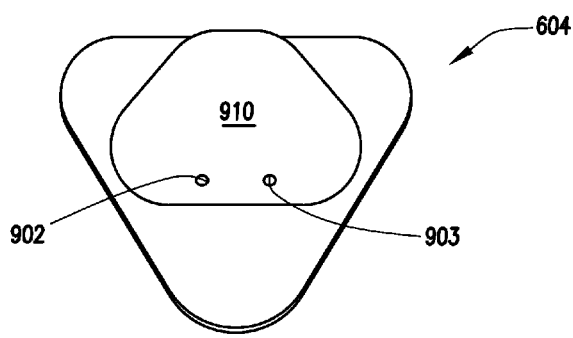

FIG. 33 illustrates one aspect of a body associated device configured to be placed on an external topical location of a subject, such as a chest area.

DESCRIPTION

In one aspect, the present specification discloses multiple configurations of a body associated device. In various aspects, the body associated device may comprise a patch, a biocollection patch, a patch receiver, a wearable personal communication device ("personal communicator"), among others, which may be individually or collectively referred to herein as a "patch," without limitation. In one aspect, a body associated device is attached to the body of a living subject and is in communication with the living subject. In one aspect, the body associated device also may be in communication with a local node external to the body of the living subject. The local node may be any form of communication node and may comprise hardware and/or software components working alone or in combination. In one aspect, the local node is in communication with a remote node via a network and, accordingly, the living subject is able to communicate with the remote node. Information also may be communicated from the remote node and/or the local node to the living subject via the body associated device. In one aspect, the remote node may comprise a computer or server configured to communicate information with the body associated device and/or to store, manipulate, process, and manage information received from and sent to the body associated device.

In another aspect, the present specification discloses one or more configurations of a body associated device that comprises, for example, alone or in combination, a sectioned housing, a tiered housing, a flexible housing, hydrogel pockets, base layer that removes stiffness, multiple components assembled together, air pockets to allow better adhesion to the body of a living subject, tiered pockets to allow expansion of hydrogel away from the skin of the living subject, and various body compliant or preformed body curved form factor to enhance better fitment to the body of the living subject.

In other aspects, the present specification discloses one or more configurations of a body associated device that comprises alone or in combination, for example, the features previously described and enclosures or housing formed of various materials. In one aspect, the enclosure may be formed of materials having suitable flexibility to enable actuation of a button switch beneath the housing. In other aspects, the enclosure may be formed of a translucent material to enable energy, e.g., light, sound, etc., emitted by electronic components discernable to the living subject or detectable by other electronic components external to the housing. In other aspects, flexible electronic printed circuits are provided for electrodes and electrical connections. For example, a flexible electronic printed circuit can provide a significant amount of flexibility in contrast to standard electrode configurations. In other aspects, the body associated device comprises a laminated-type design suitable to support manufacturing processes, such as high volume manufacturing processes. In one example, the laminated design is suitable for high volume web manufacturing where a long, thin, and flexible material including foil, metal, paper, textile, plastic, and wire are generally processed by moving over rollers. One advantage of working with webs is economics. Webs, being continuous, can be made at far higher speeds and do not have the start-stop issues of discrete sheet processing. Web processing is also found in a wide variety of manufacturing including electronics such as circuit boards.

In other aspects, the body associated device provides a physical housing configuration comprising a smooth shape and a low profile that is comfortable to wear by the living subject. For example, in various aspects, the body associated device comprises a structural configuration that is flexible enough to enable comfortable adhesion to the body of the living subject without adding stress on the adhesion layer that would tend to pull the body associated device away from the body of the living subject. In one aspect, such flexibility and comfort may be achieved by reducing the amount of stiffness in the structure of the body associated device, such as the stiffness of the housing and/or other components. Such flexibility may be achieved by patch design, material selection, reduction in stiff sections, and reduction in size and weight of the body associated device.

In other aspects, the body associated device provides a waterproof fluid tight housing in accordance with IEC 60529 IPX7 specifications. Accordingly, in various aspects, the body associated device can withstand a predefined level of submersion in a fluid (e.g., water) without enabling the fluid to access the electronic components of the body associated device.

In other aspects, the body associated device comprises a skin or body adhesive layer that provides a strong adhesive connection to the body of the living subject that is suitable for holding the body associated device attached to the living subject during a wear period of, for example, 1 to 3 days, 3 to 7 days, 7 to 14 days, 7 to 21 days, and so on. Such functionality may be achieved, for example, by material selection, design and shape of the adhesion area as well as the location of application to the body of the living subject. In other aspects, the adhesive layer may be selected to provide a non-irritating connection/adhesion to the body of the living subject by selecting suitable biocompatible materials and skin adhesives.

In other aspects, the body associated device provides assembly features that enhance and create a flexible connection between the body of the living subject and the body associated device patch. In one aspect, the body associated device comprises foam or other flexible elements, e.g., in the form of a ring, that connect the skin adhesive to a bottom layer of the body associated device housing (enclosure). In various aspects, such features enable the larger skin adhesive layer to breathe and manage absorption and release of fluid (water, perspiration) during wear. In contrast, if the entire bottom surface area of the body associated device was adhered to the skin of the living subject, it would establish large areas of adhesion that would not be able to breathe as much and would be likely to cause earlier delamination of the body associated device patch from the skin. In one aspect, adhesive rings without the flexible foam layer may be employed to join the body associated device patch to the body of the living subject. Such aspect would provide a breathable connection without the additional thickness of the flexible foam ring material.

In other aspects, the body associated device provides electrical connections (resistive, capacitive, inductive) to the body of the living subject to enable the capture of electrical signals (ECG, EKG, EMG, IEM) from the living subject. The electrical connection may be implemented by employing a conductive material that enables an electrical connection to the body of the living subject while retaining fluid protection. The electrical connection can be provided, for example, by employing Ag/AgCl electrodes with a hydrogel interface to the skin of the living subject. It also can be enabled by employing dry electrodes, which provide a suitable stable connection to the body of the living subject as described in PCT Patent Application No. PCT/US11/23017 dated Jan. 28, 2011 titled "TWO-WRIST DATA GATHERING SYSTEM" and in PCT Patent Application No. PCT/US11/23013 dated Jan. 28, 2011 titled "DATA GATHERING SYSTEM," in which the disclosure of each is herein incorporated by reference in its entirety.

The various aspects of a body associated device are described hereinbelow in connection with the figures.

Figure 1:
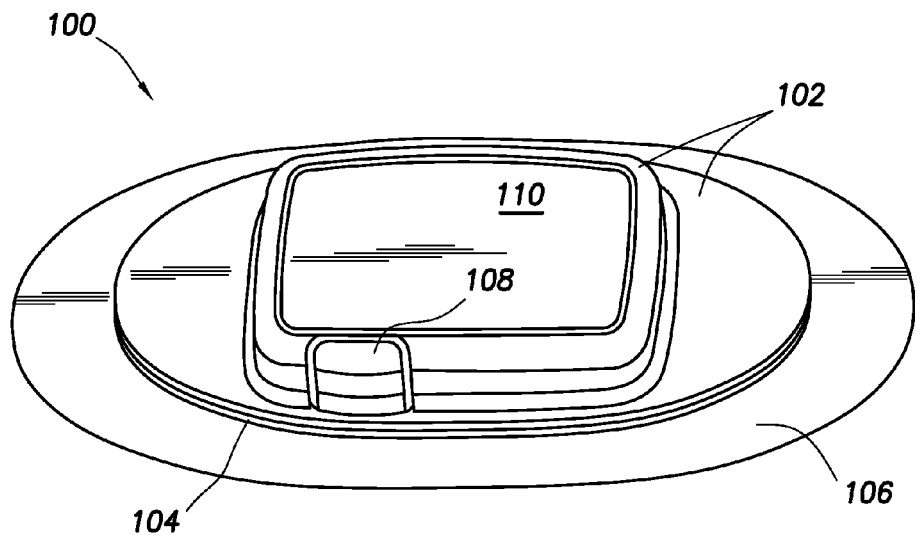
FIG. 1 is a perspective view of one aspect of a body associated device.

FIG. 1 is a perspective view of one aspect of a body associated device 100. In various aspects the body associated device 100 may be implemented as a patch, a biocollection patch, a patch receiver, a wearable personal communication device ("personal communicator"), among others, which may be individually or collectively referred to herein as a "patch," without limitation. The patch 100 comprises a housing 102 (e.g., enclosure), a flexible layer 104, and an adhesive layer 106. In one aspect, the illustrated patch 100 also comprises a flexible feedback portion 108. In one aspect, the flexible feedback portion 108 may be formed separately (as shown) or integrally within the housing 102. Although the flexible feedback portion 108 may serve multiple functions, in one aspect, the flexible feedback portion 108 may be employed in a manner to enable the living subject to communicate with electronic modules located within the housing 102 of the patch 100. For example, in one aspect the flexible feedback module 108 is coupled to a push button switch, such as, for example, the pushbutton switch 140 shown in FIGS. 17, 18. With reference now back to FIG. 1, in one aspect, the patch 100 may comprise a top portion 110 to receive some form of indicia such as a logo, advertising, or label. The housing 102 may be attached to the flexible layer 104 using any suitable fastening technique including, for example, using adhesive, glue, epoxy, silicone, ultrasonic welding, rivets, screws, clips, snaps, etc.

In various aspects, the housing 102 may be formed in one or more configurations. In various aspects, the housing 102 may comprise a sectioned portion, a tiered portion, a flexible housing, hydrogel pockets, base layer that removes stiffness, multiple components assembled together, air pockets to allow better adhesion to the body of a living subject, tiered pockets to allow expansion of hydrogel away from the skin of the living subject, and various body compliant or pre-formed body curved form factor to enhance better fitment to the body of the living subject. A number of these housing configurations will be described in more detail hereinbelow.

In other aspects, the housing 102 or enclosure may be formed of various materials. In one aspect, the housing 102 may be formed of materials having suitable flexibility to enable actuation of a flexible push button switch located beneath the housing 102. Such configuration reduces component count and provides a suitable for waterproof/water-tight construction to support water ingress prevention. In other aspects, the housing 102 may be formed of a translucent material to enable light emitted by electronic components visible to the living subject or detectable by other electronic components external to the housing 102. Such configuration also reduces parts count and provides a suitable waterproof/watertight construction to support water ingress prevention. In other aspects, flexible electronic printed circuits are provided for electrodes and electrical connections. For example, a flexible electronic printed circuit can provide a significant amount of flexibility in contrast to standard electrode configurations. In other aspects, the patch 100 comprises a laminated-type design suitable to support high volume web manufacturing processes.

In other aspects, the patch 100 comprises a physical housing 102 configuration comprising a smooth shape and a low profile that is comfortable to wear by the living subject. As shown in FIG. 1, the housing 102 comprises rounded corners and the portion comprises a radius of curvature. Also, the aspect ratio of the housing 102 is selected to provide a low profile. For example, in various aspects, the housing 102 comprises a structural configuration that is flexible enough to enable comfortable adhesion to the body of the living subject without adding stress on the adhesion layer that would tend to pull the body associated device away from the body of the living subject. In one aspect, such flexibility and comfort may be achieved by reducing the amount of stiffness in the structure of the patch 100, such as the stiffness of the housing and/or other components. Such flexibility may be achieved by patch design, material selection, reduction in stiff sections, and reduction in size and weight of the body associated device.

In other aspects, the housing 102 portion of the patch 100 provides a waterproof fluid tight housing in accordance with IEC 60529 IPX7 specifications. It will be appreciated that IEC 60529 is a European system of test specification standards for classifying the degrees of protection provided by the enclosures of electrical equipment. An IPX7 designation means the patch 100 housing 102 can withstand accidental immersion in one meter of water for up to 30 minutes. An IPX8 designation is for continuous underwater use. Accordingly, in various aspects, the patch 100 can withstand a predefined level of submersion in one meter of water for up to 30 minutes without enabling the fluid to access the electronic components of the patch 100.

In various aspects, the housing 102 may be formed of a variety of polymers. For example, the housing 102 may be formed of plastics either thermoplastics or thermosetting polymers. Thermoplastics are the plastics that do not undergo chemical change in their composition when heated and can be molded multiple times. Examples of thermoplastics include polyethylene, polystyrene, polyvinyl chloride (PVC), polytetrafluoroethylene (PTFE). Other polymers include synthetic rubber, Bakelite, neoprene, nylon, polypropylene, polyacrylonitrile, polyvinyl butyral (PVB), silicone, acrylates, and many more. Thermosetting plastics can melt and take shape once. After they have solidified, they stay solid. The housing 102 may be formed of other suitable polymers including, without limitation, natural polymeric materials such as shellac, amber, natural rubber, and cellulose, which is the main constituent of wood and paper. It will be appreciated that the housing 102 also may be formed of other suitable non-polymeric materials such as aluminum or other lightweight durable metal.

In one aspect, the adhesive layer 106 is pressure sensitive and is configured to be applied to the skin of the living subject. In various aspects, the adhesive layer 106 provides a strong adhesive connection to the body of the living subject that is suitable for holding the patch 100 attached to the living subject during a wear period of, for example, 1 to 3 days, 3 to 7 days, 7 to 14 days, 7 to 21 days, and so on. Such functionality may be achieved, for example, by material selection, design and shape of the adhesion area as well as the location of application to the body of the living subject. In other aspects, the adhesive layer 106 may be selected to provide a non-irritating connection/adhesion to the body of the living subject by selecting suitable biocompatible materials and skin adhesives. Examples of such biologically compatible skin adhesive include, without limitation, any skin adhesive that will successfully maintain the adherence of a dermal dressing to moist (perspiring) skin on a living subject working in hot humid environments, without producing adverse reactions such as rashes and itching. In one aspect, the biologically compatible skin adhesive comprises synthetic emulsions acrylic copolymers which are odorless and pressure sensitive. Such water-insoluble adhesives may comprise hydrophilic units to permit strong bonding to wet human skin and still retain some water resistance to permit durability.

The copolymer may be prepared to achieve better wet tack and water resistance, peel adhesion and peel adhesion as a function of rate, and may not contain any residual monomer, which is a potential source of skin irritation. In addition, the adhesion layer 106 comprises rounded edges, or other suitable designs befitting the curvature of other parts of the body which further reduce peeling discomfort from the skin as compared to sharp edges.

Figure 2:
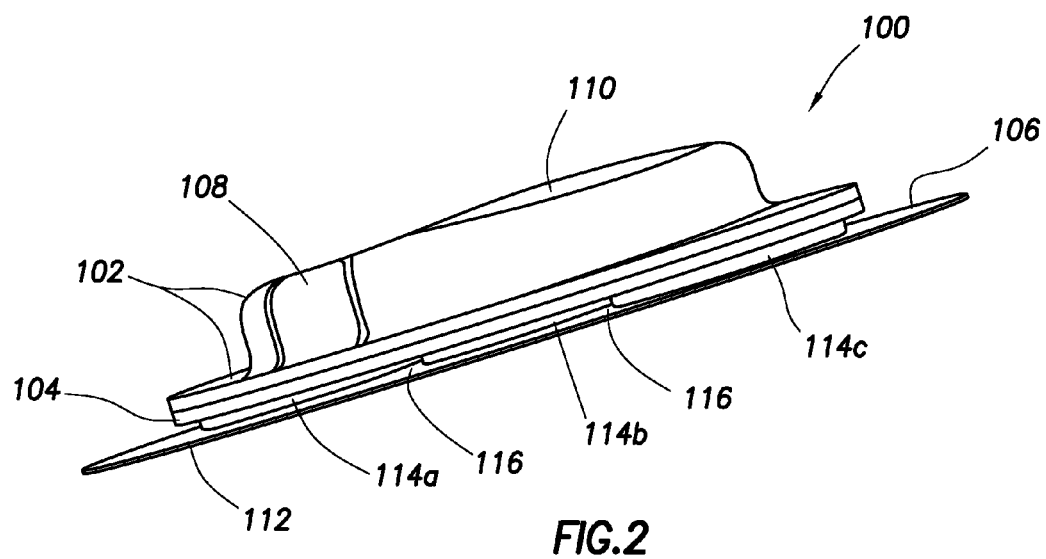
FIG. 2 is a perspective view of one aspect of the body associated device shown in FIG. 1.
Figure 29A:
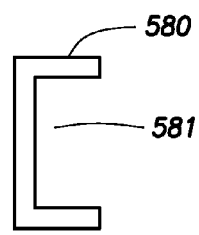
Figure 29B:
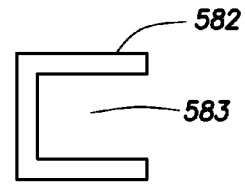
Figure 29C:
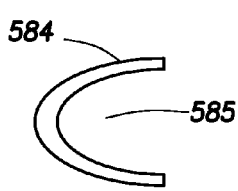
Figure 29D:
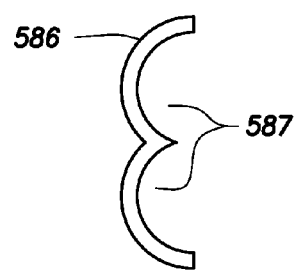

FIG. 2 is a perspective view of one aspect of the body associated device shown in FIG. 1. As shown in FIG. 2, the patch 100 further comprises a liner 112 to protect the adhesive layer 106 before the patch 100 is applied to the body of the living subject. In use, the liner 112 is peed off the adhesive layer 106 before the patch 100 is applied to the body of the living subject. In the aspect of the patch 100 illustrated in FIG. 2, the patch 100 further comprises a first outer standoff 114a, an inner standoff 114b, and a second outer standoff 114c. In one aspect, the standoffs 114a-c are ring shaped, e.g., a circular band or continuous outer portion defining an inner aperture or space therein, and have a predetermined thickness (see e.g., standoffs 114a-c in FIG. 12). In other aspects, in addition to the circular ring shape of the standoffs 114a-c, the standoffs may be formed in any suitable shape such as square, rectangle, oval, kidney, where each of the shapes includes a continuous solid outer portion that defines an inner aperture or space as shown in FIGS. 29A-D. In still other aspects, the standoffs may have a broken shape. For example, the broken standoff has a broken outer portion with an open portion in the form of a "C," as shown in FIG. 29A-C, or an "E," as shown in FIG. 29D. Although not shown, in one aspect, the circular ring shaped standoffs 114a-c can be formed in a broken "C" like shape.

With reference now back to FIG. 2, accordingly, each of the standoffs 114a-c define a continuous outer portion defining a corresponding inner space or aperture inside the ring. The standoffs 114a-c may be attached to the flexible layer 104 using any suitable fastening techniques including, for example, using adhesive, glue, epoxy, silicone, ultrasonic welding, rivets, screws, clips, snaps, etc. In one aspect, the standoffs 114a-c may be formed of a foam material that includes adhesive on one side or on both sides of the foam material. In one aspect, the standoffs 114a-c have a thickness ranging from about 0.1 mm to about 3 mm. The liner 112 may be attached to the standoffs 114a-c using any suitable fastening technique including, for example, adhesive, glue, epoxy, silicone, ultrasonic welding, etc.

In other aspects, the patch 100 provides assembly features that enhance and create a flexible connection between the body of the living subject and the patch 100. In one aspect, the flexible layer 104 of the patch 100 comprises foam or other flexible elements, e.g., in the form of rings, that connect the skin adhesive to a bottom layer of the body associated device housing (enclosure). In various aspects, the standoffs 114a-c are formed in ring shape from a foam or other flexible material. In various aspects, the standoffs 114a-c enable the larger skin adhesive layer 106 to breathe and manage absorption and release of fluid (water, perspiration) during wear by providing air gaps 116 between the flexible layer 104 and the adhesive layer 106. The flexible layer 104 alone has a tendency to cause condensation on the skin of the living subject. The standoffs 114a-c provide reduced contact area with the skin and also provide some additional flexibility. The standoffs 114a-c are able to stretch and give because the movement of the standoffs 114a-c is not confined to the area of the flexible layer 104 and thus the patch 100 is more stretchable with the skin. In contrast, if the entire bottom surface area of the patch 100 was adhered to the skin of the living subject, it would establish large areas of adhesion that would not be able to breathe as much and would be likely to cause earlier delamination of the patch 100 from the skin. Permeable materials provide a moisture vapor transition rate (MVTR) and adhere better to the skin. In one aspect, the adhesive layer 106 may be formed as adhesive rings without the foam flexible layer 104. The adhesive layer 106 may be employed to join the patch 100 to the body of the living subject. Such aspect would provide a breathable connection without the additional thickness of the flexible foam ring material of the standoffs 114a-c. In one aspect, the flexible layer 104 is interposed between the standoffs 114a-c and the housing 102. In various aspects, the attachment points between the patch 100 and the skin of the living subject may be determined by the shape of the standoffs 114a-c. For example, in various aspects, the number of attachments points can be anywhere from 1 to 10 or many more than 10.

Figure 3:
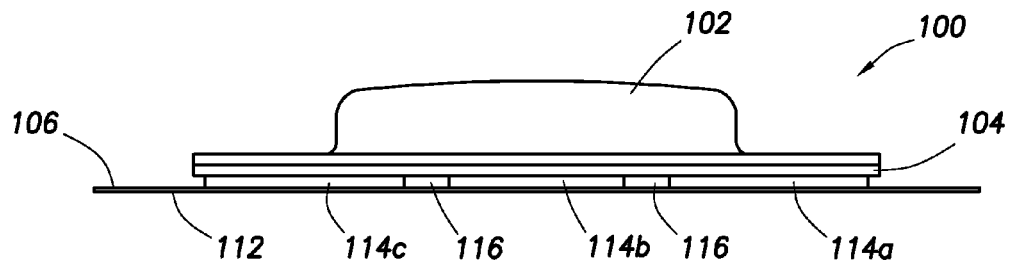
FIG. 3 is a rear view of one aspect of the body associated device shown in FIG. 1.
Figure 4:
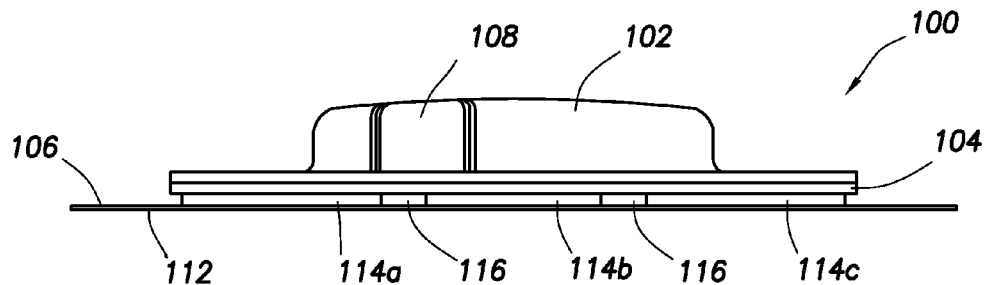
FIG. 4 is a front view of one aspect of the body associated device shown in FIG. 1.
Figure 5:
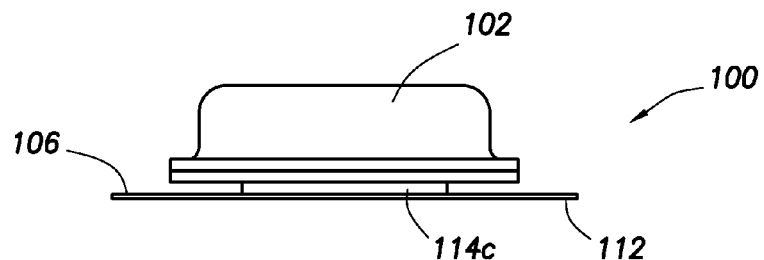
FIG. 5 is a side view of one aspect of the body associated device shown in FIG. 1.
Figure 6:
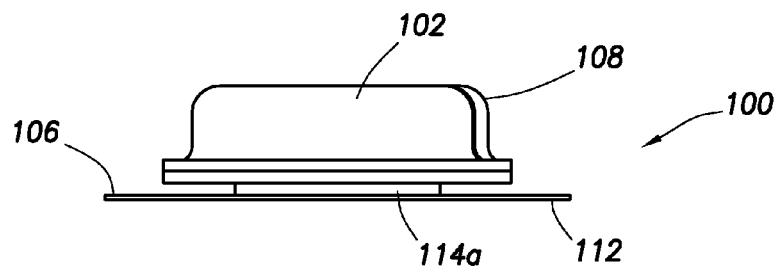
FIG. 6 is another side view of one aspect of the body associated device shown in FIG.

FIG. 3 is a rear view of the patch 100. FIG. 4 is a front view of the patch. FIGS. 5 and 6 are side views of the patch 100. The aspects of the patch 100 illustrated in FIGS. 1-6 show the standoffs 114a-c and the air gaps 116. As shown, an air gap 116 is defined between the first outer standoff 114a and the inner standoff 114b and another air gap 116 is defined between the inner standoff 114b and the second outer standoff 114c.

Figure 7:
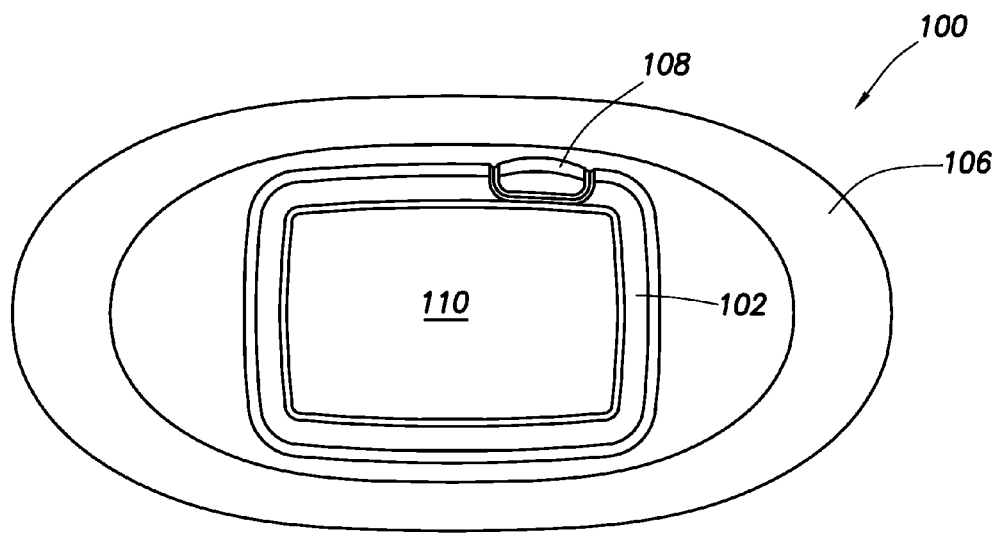
FIG. 7 is a top view of one aspect of the body associated device shown in FIG. 1.
Figure 8:
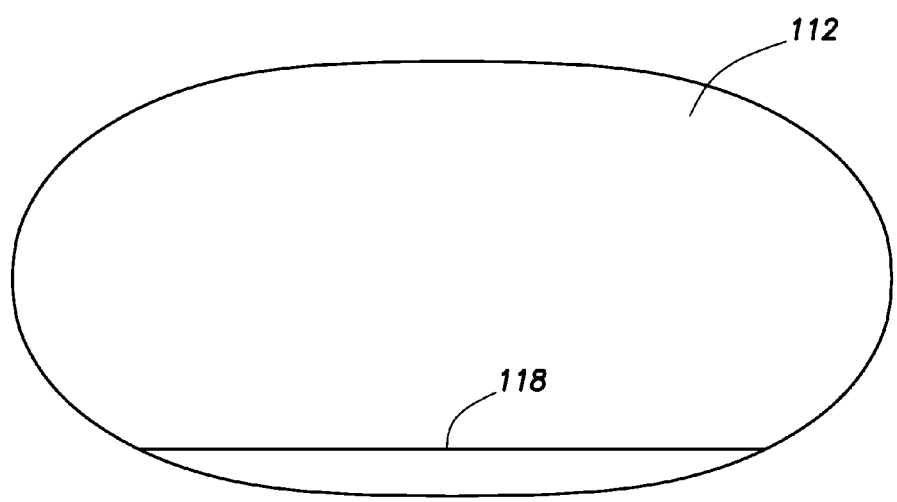
FIG. 8 is a bottom view of one aspect of the body associated device shown in FIG. 1.

FIG. 7 is a top view of the patch 100 and FIG. 8 is a bottom view of the patch 100 with the liner 112 still in place. As shown, in FIG. 8, in one aspect the liner 112 comprises a liner seam 118 to enable easy removal of the liner 112 from the adhesive layer 106 (FIGS. 1-7).

Figure 9:
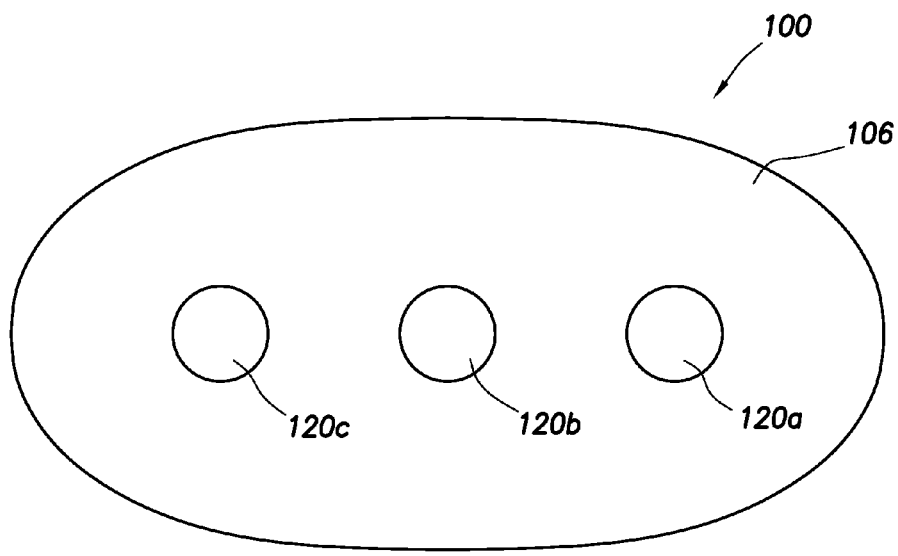
FIG. 9 is a bottom view of one aspect of the body associated device shown in FIG. 1 with an adhesive liner layer removed.

FIG. 9 is a bottom view of one aspect of the patch 100 with the adhesive liner 112 layer removed. As shown, the liner 112 layer having been removed, the adhesive layer is shown 106. Three apertures are now revealed. A first inner aperture 120a opens into the inner space defined by the first outer standoff 114a (FIGS. 2-4, 6). A second inner aperture 120b opens into the inner space defined by the inner standoff 114b (FIGS. 2-4). A third inner aperture 120c opens into the inner spaced defined by the second outer standoff 114c (FIGS. 2-4, 5).

Figure 10:
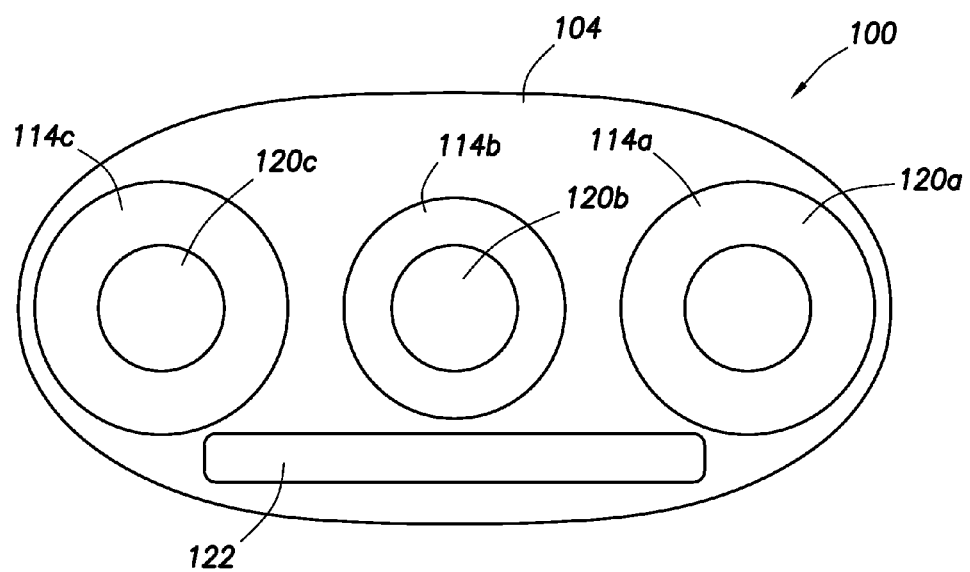
FIG. 10 is a bottom view of one aspect of the body associated device shown in FIG. 1 with the adhesive liner and skin base adhesive layers removed.
Figure 11:
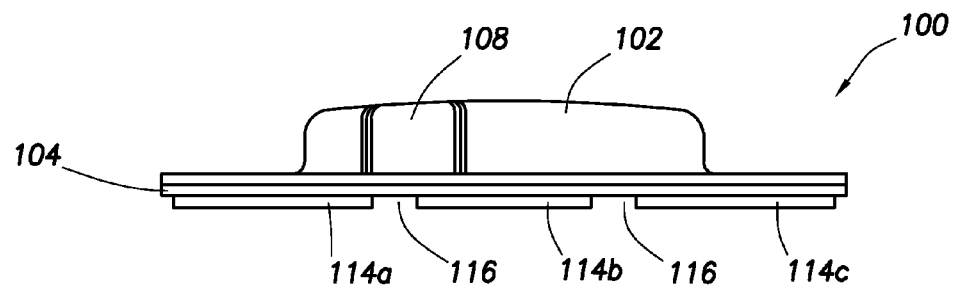
FIG. 11 is a side view of one aspect of the body associated device shown in FIG. 10 with the adhesive liner and skin base adhesive layers removed.
Figure 12:
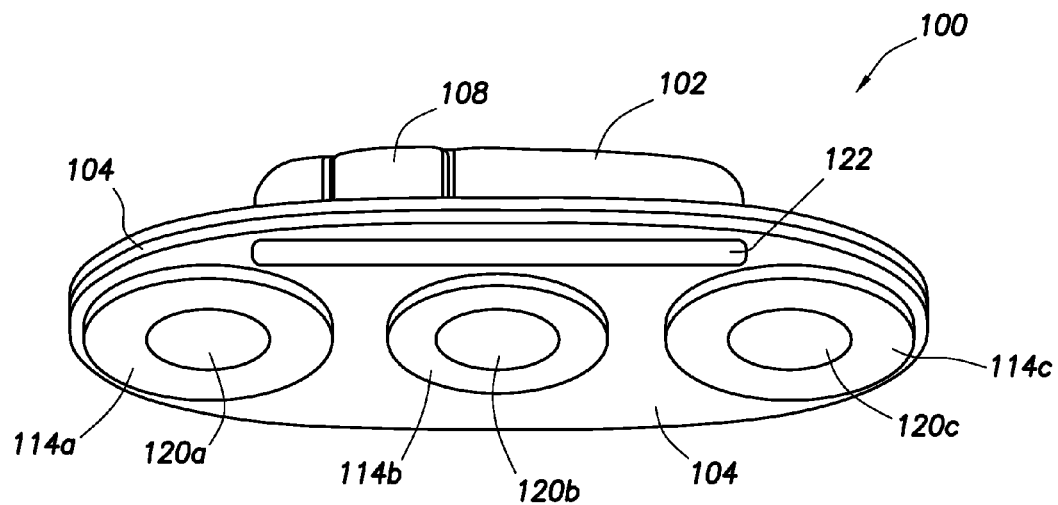
FIG. 12 is a perspective view of one aspect of the body associated device shown in FIG. 11 with the adhesive liner and skin base adhesive layers removed.

FIG. 10 is a bottom view of one aspect of the patch 100 with the adhesive liner 112 and skin base adhesive layer 106 removed. FIG. 11 is a side view of one aspect of the patch 100 shown in FIG. 10 with the adhesive liner 112 and skin base adhesive layer 106 removed. FIG. 12 is a perspective view of one aspect of the patch 100 shown in FIG. 11 with the adhesive liner 112 and skin base adhesive layer 106 removed. With reference now to FIGS. 10-12, with the liner 112 and adhesive layer 106 removed, the structure of the outer standoffs 114a-c can be seen. As shown, the inner apertures 120a-c defined by corresponding standoffs 114a-c are used to hold the hydrogel and electrically couple the electrodes to the skin of the living subject. A data label 122 is provided to display any suitable type of information.

With reference now to FIGS. 9-12, as will be defined in more detail below, in various aspects, the patch 100 provides electrical connections (resistive, capacitive, inductive) to the body of the living subject to enable the capture of electrical signals (ECG, EKG, EMG, IEM), conductive signals, irradiative signals, etc., from the living subject. The electrical connection may be implemented by employing a conductive material that enables an electrical connection to the body of the living subject while retaining fluid protection. The electrical connection can be provided, for example, by employing Ag/AgCl electrodes with a hydrogel interface to the skin of the living subject. It also can be enabled by employing dry electrodes, which provide a suitable stable connection to the body of the living subject. Accordingly, prior to adhering the patch 100 to the skin of the living subject, the inner apertures 120a-c defined by the standoffs 114a-c are filled with a hydrogel conductive fluid, which is used to electrically couple the body of the living subject to electrodes located within the patch 100. A hydrogel (also called aquagel) is a network of polymer chains that are hydrophilic and is commonly used in medical electrodes. Such medical electrode hydrogels are composed of cross-linked polymers such as polyethylene oxide, poly(2-acrylamido-2-methyl-1-propanesulfonic acid (polyAMPS), and polyvinylpyrrolidone, for example. The hydrogel can be placed into the inner apertures 120a-c either at the time of manufacture, prior to the application of the liner 112 to the adhesive layer 106 or can be placed in the inner apertures 120a-c by the living subject after removing the liner 112 from the adhesive layer 106 just before applying the patch 100 to the skin.

Figure 13:
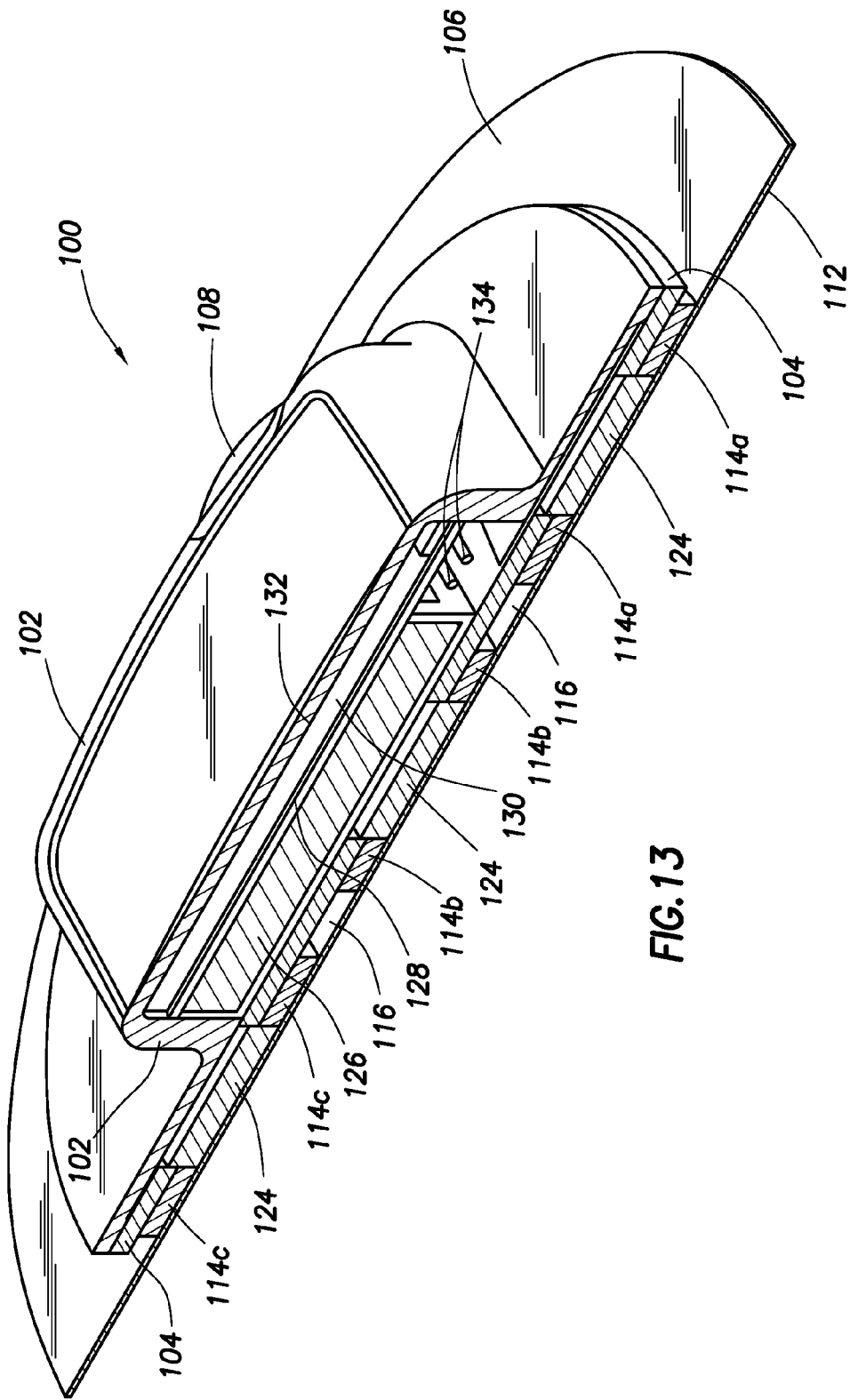
FIG. 13 is a perspective sectional view of one aspect of the body associated device shown in FIG. 1.
Figure 14:
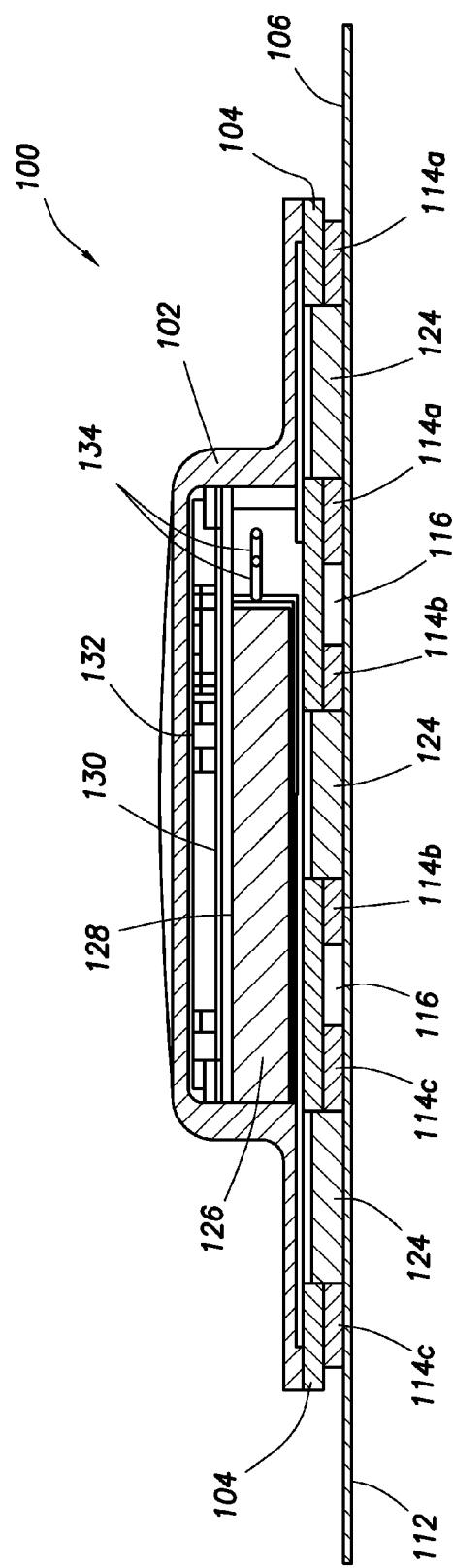
FIG. 14 is a sectional side view of one aspect of the body associated device shown in FIG. 13.
Figure 15:
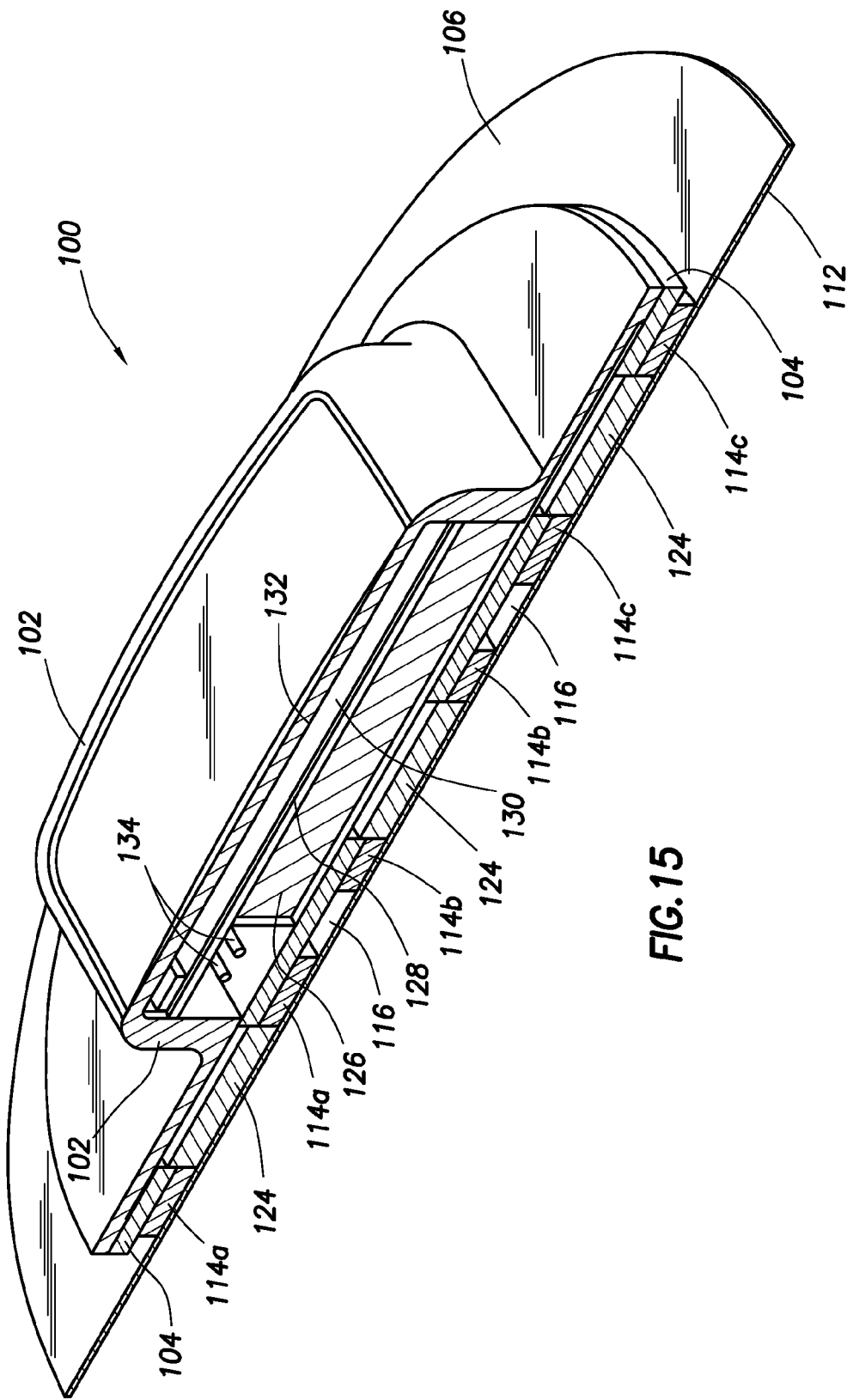
FIG. 15 is a perspective sectional view of one aspect of the body associated device shown in FIG. 1.
Figure 16:
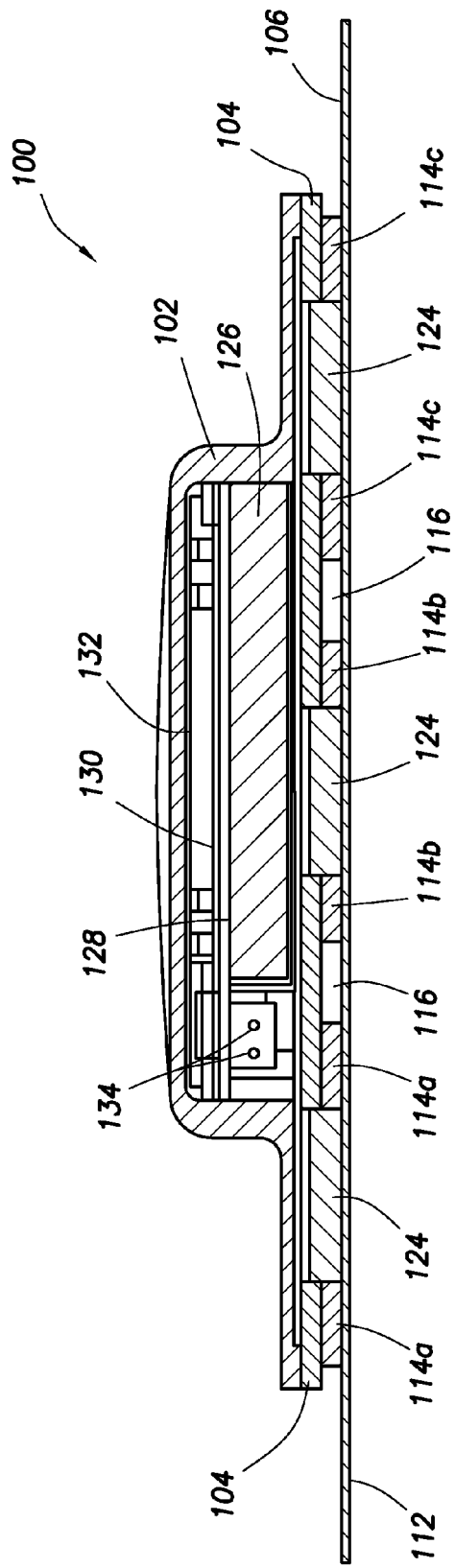
FIG. 16 is a sectional side view of one aspect of the body associated device shown in FIG. 15.

FIG. 13 is a perspective sectional view of one aspect of the patch 100 shown in FIG. 1. FIG. 14 is a sectional side view of one aspect of the patch 100 shown in FIG. 13. FIG. 15 is a perspective sectional view of one aspect of the patch 100 shown in FIG. 1. FIG. 16 is a sectional side view of one aspect of the patch 100 shown in FIG. 15. With reference now to FIGS. 13-16, the patch 100 comprises an electronic module located within the housing 102. Also in the aspect of the patch 100 shown in FIGS. 13-16, the patch 100 comprises electrode hydrogel 124 located in the space defined by the standoffs 114a-c. Furthermore, the patch 100 comprises a battery 126 and a printed circuit board 128. In one aspect, the printed circuit board 128 is a flexible printed circuit design for electrodes and connections. The thin flexible printed circuit board 128 substrate material provides suitable flexibility in contrast to conventional electrode designs. The battery powers the electronic module and the circuit board 128 contains the electronic components of the electronic module. An isolation film 130 electrically isolates the printed circuit board 128 from an electrostatic discharge (ESD) shield 132. The ESD shield 132 protects the electronic circuit components located on the printed circuit board 128 from electrostatic discharge and/or electromagnetic interference. Pin sockets 134 electrically connect a pushbutton switch to a header.

Figure 17:
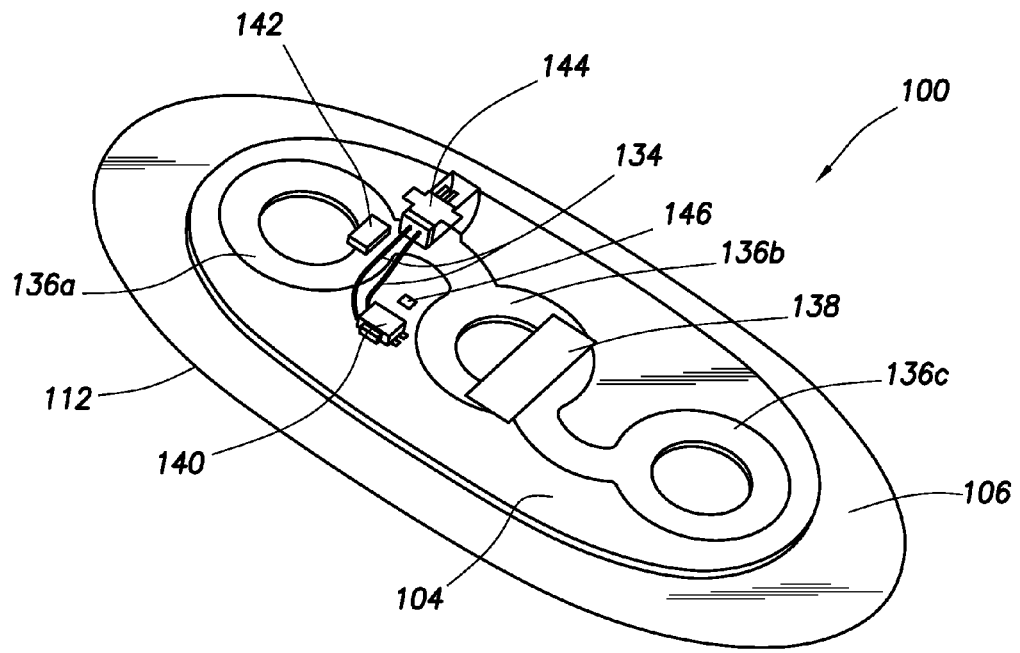
FIG. 17 is a perspective view of one aspect of the body associated device shown in FIG. 1 with a housing cover and functional electronic components removed.
Figure 18:
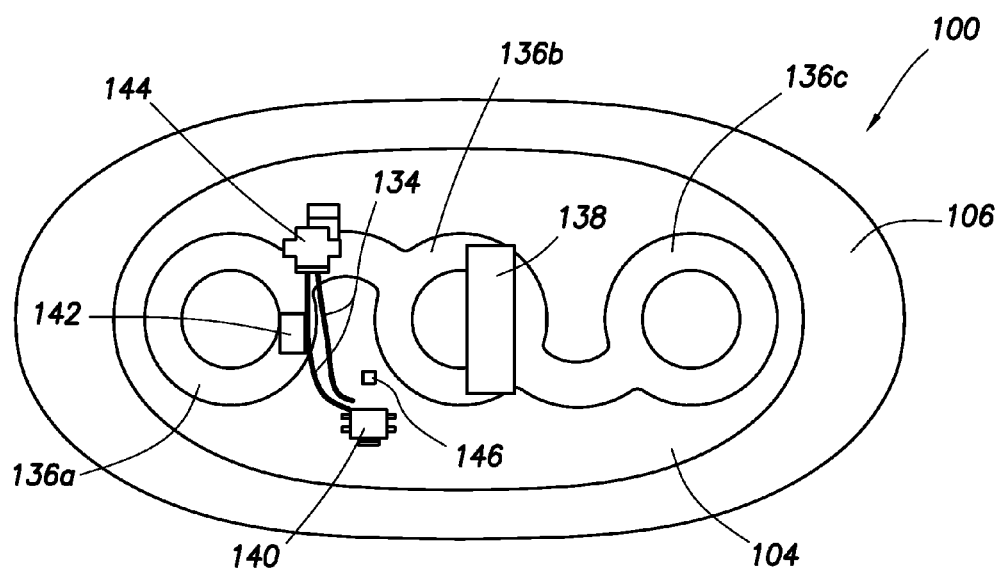
FIG. 18 is a top view of one aspect of the body associated device shown in FIG. 17 with the housing cover and functional electronic components removed.

FIG. 17 is a perspective view of one aspect of the patch 100 with the housing cover 102 and functional electronic components removed. FIG. 18 is a top view of the patch 100 shown in FIG. 17 with the housing cover 102 and functional electronic components removed. With the housing 102 and functional electronic components removed, it can be seen that the patch 100 includes a conductive element such as, for example, a conductive electrode. In one aspect, the conductive element is flexible and forms a flexible electrode circuit. Although it may form part of the same circuit, the flexible electrode circuit is referenced as three portions of the conductive flexible electrode circuits 136a, 136b, 136c, which correspond to the inner apertures 120a-c and the standoffs 114a-c. The conductive flexible electrode circuits 136a-c are located above the corresponding standoffs 114a-c, located below the foam flexible layer 104. In addition, the patch 100 comprises a water ingress indicator 138 to detect water or moisture penetration into the housing 102 (not shown in FIGS. 17, 18). A pushbutton switch 140 is provided to receive input commands for the living subject. The pin sockets 134 are electrically coupled to the pushbutton switch 140 and to a header 144 socket. An antenna 142 is provided for communication between the patch 100 and the local node and/or the remote node. In one aspect, the electronic module comprises a transceiver coupled to the antenna 142. The antenna 142 and transceiver enable wireless communications between the electronic module and external local/remote nodes and/or receive information from the local/external nodes. An indicator, e.g., a light source 146 such as a light emitting diode (LED) is provided to indicate status and control information associated with the patch 10 and/or the living subject.

In various aspects, the patch 100 provides electrical connections (resistive, capacitive, inductive) to the body of the living subject to enable the capture of electrical signals (ECG, EKG, EMG, IEM) from the living subject. The electrical connection may be implemented by employing a conductive material such as the electrode hydrogel 124 (FIGS. 13-16) and flexible electrode circuits 136a-c that enables an electrical connection to the body of the living subject while retaining fluid protection. In one aspect, the electrical connection can be provided, for example, by employing Ag/AgCl flexible electrode circuits 136a-c with a hydrogel 124 interface to the skin of the living subject. It also can be enabled by employing dry electrodes, which provide a suitable stable connection to the body of the living subject.

Figure 19:
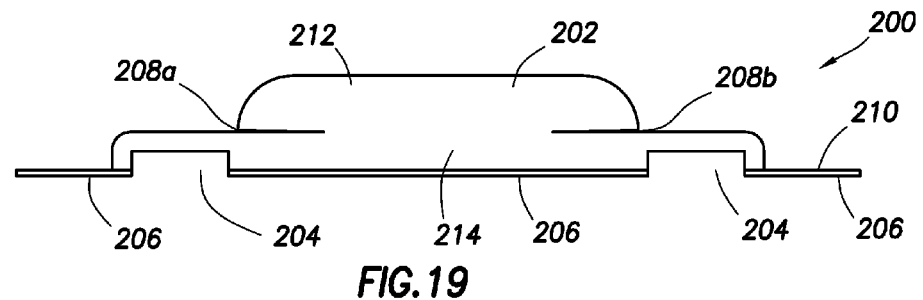
FIG. 19 is a side sectional view of one aspect of a body associated device.

FIG. 19 is a side sectional view of one aspect of a body associated device 200. In various aspects the body associated device 200 may be implemented as a patch, a biocollection patch, a patch receiver, a wearable personal communication device ("personal communicator"), among others, which may be individually or collectively referred to herein as a "patch," without limitation. The patch 200 comprises a sectioned/tiered housing 202 for flexibility, a base layer 210, and pockets 204 defined by the housing 202. The pockets 204 are configured to receive electrode hydrogel therein. The housing 202 comprises a top portion 212 and a flexible bottom portion 214. The top portion 212 and the flexible bottom portion 214 define at least one slot to remove stiffness and enable the housing 202 to flex. In the illustrated housing 202, slots 208a, 208b defined by the top and bottom portions 212, 214 of the housing 202 remove housing stiffness when the housing is flexed. An adhesive layer 206 is provided to adhere the patch 200 to the body of the living subject.

Figure 20:
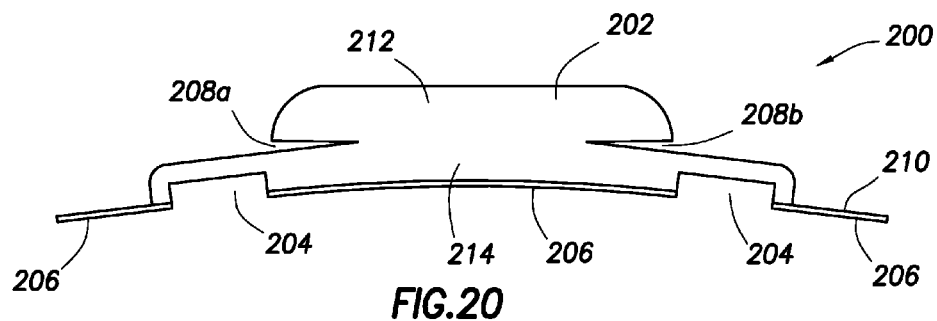
FIG. 20 is a side sectional view of one aspect of the body associated device shown in FIG. 19 in a flexed configuration.

FIG. 20 is a side sectional view of one aspect of the patch 200 shown in FIG. 19 in a flexed configuration. As shown, the top portion 214 of the housing 202 remains substantially in the same configuration whether or not the housing 202 is flexed. The flexible portion 214 flexes and conforms to the contours of the body of the living subject. The slots 208a, b provide the necessary flexibility to remove the stiffness of the housing 202.

Figure 21:
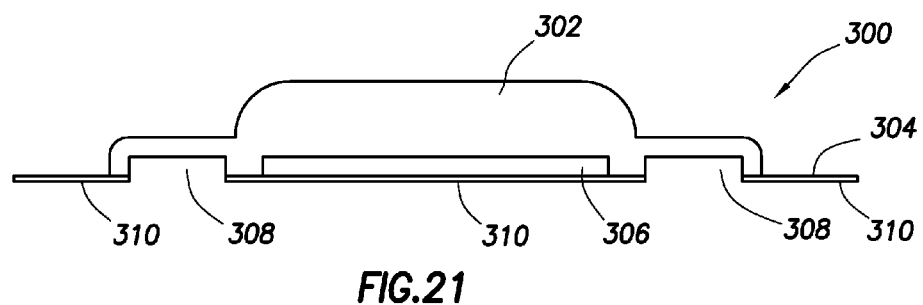
FIG. 21 is a side sectional view of one aspect of a body associated device.

FIG. 21 is a side sectional view of one aspect of a body associated device 300. In various aspects the body associated device 300 may be implemented as a patch, a biocollection patch, a patch receiver, a wearable personal communication device ("personal communicator"), among others, which may be individually or collectively referred to herein as a "patch," without limitation. The patch 300 comprises a housing 302, a base layer 304, and pockets 308 defined by the housing 302. The pockets 308 are configured to receive electrode hydrogel therein. An adhesive layer 310 is provided to adhere the patch 300 to the body of the living subject. The housing 302 also includes an airgap 306 to allow for better adhesion of the adhesive layer 310 to the body of the living subject. The airgap 306 may be formed as a pattern in the lower foam/flexible layer of the housing 302 to reduce adhesive contact to the adhesive layer 310 to allow water vapor permeation through the base layer 304.

Figure 22:
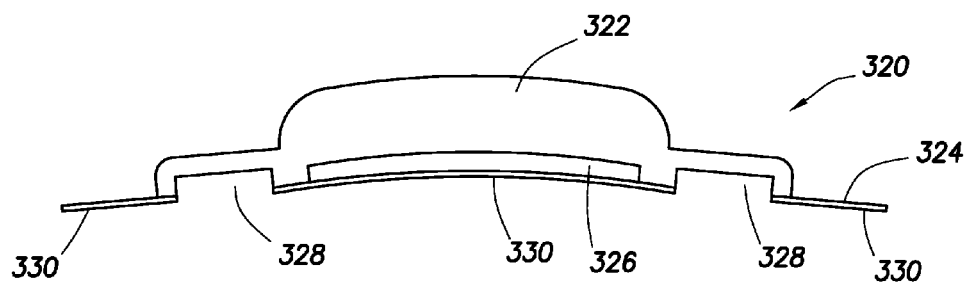
FIG. 22 is a side sectional view of one aspect of a form fitting preformed body associated device.

FIG. 22 is a side sectional view of one aspect of a form fitting preformed body associated device 320. In various aspects the body associated device 320 may be implemented as a patch, a biocollection patch, a patch receiver, a wearable personal communication device ("personal communicator"), among others, which may be individually or collectively referred to herein as a "patch," without limitation. The patch 320 comprises a preformed housing 322, a base layer 324, and pockets 328 defined by the housing 322. The preformed housing 322 comprises a preformed body form factor with a curvature to conform to the contours of the body of the living subject to enhance better fitment to the body of the living subject. The pockets 328 are configured to receive electrode hydrogel therein. An adhesive layer 330 is provided to adhere the patch 320 to the body of the living subject. The preformed housing 322 also includes an airgap 326 to allow for better adhesion of the adhesive layer 330 to the body of the living subject. The airgap 326 may be formed as a pattern in the lower foam/flexible layer of the preformed housing 322 to reduce adhesive contact to the adhesive layer 330 to allow water vapor permeation through the base layer 324.

Figure 23:
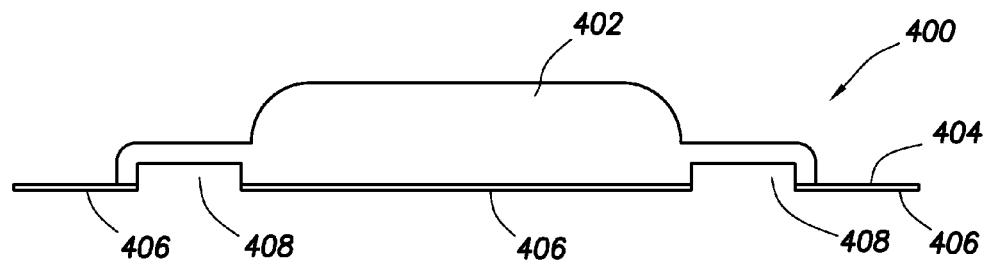
FIG. 23 is a side sectional view of one aspect of a body associated device.

FIG. 23 is a side sectional view of one aspect of a body associated device 400. In various aspects the body associated device 400 may be implemented as a patch, a biocollection patch, a patch receiver, a wearable personal communication device ("personal communicator"), among others, which may be individually or collectively referred to herein as a "patch," without limitation. The patch 400 comprises a housing 402, a base layer 404, and pockets 408 defined by the housing 402. The pockets 408 are configured to receive electrode hydrogel therein. An adhesive layer 406 is provided to adhere the patch 400 to the body of the living subject.

Figure 24:
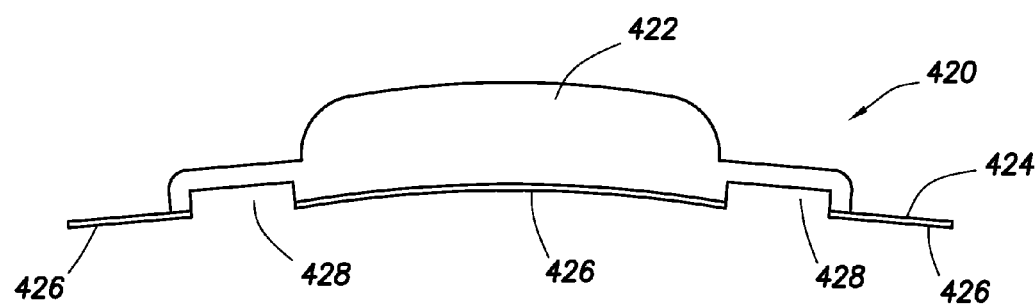
FIG. 24 is a side sectional view of one aspect of a form fitting preformed body associated device.

FIG. 24 is a side sectional view of one aspect of a form fitting preformed body associated device 420. In various aspects the body associated device 420 may be implemented as a patch, a biocollection patch, a patch receiver, a wearable personal communication device ("personal communicator"), among others, which may be individually or collectively referred to herein as a "patch," without limitation. The patch 420 comprises a preformed housing 422, a base layer 424, and pockets 428 defined by the housing 422. The preformed housing 422 comprises a preformed body form factor with a curvature to conform to the contours of the body of the living subject to enhance better fitment to the body of the living subject. The pockets 428 are configured to receive electrode hydrogel therein. An adhesive layer 426 is provided to adhere the patch 420 to the body of the living subject.

Figure 25:
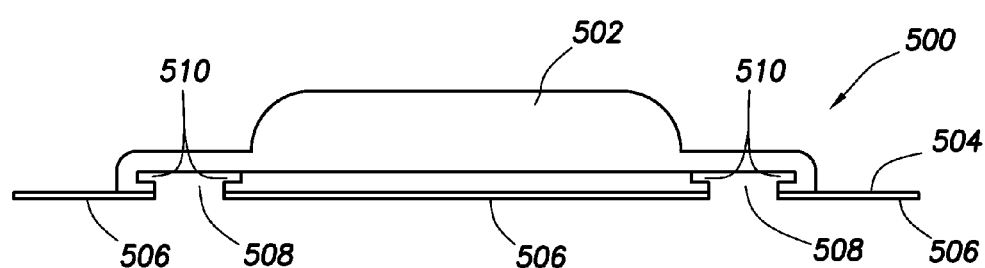
FIG. 25 is a side sectional view of one aspect of a body associated device.

FIG. 25 is a side sectional view of one aspect of a body associated device 500. In various aspects the body associated device 500 may be implemented as a patch, a biocollection patch, a patch receiver, a wearable personal communication device ("personal communicator"), among others, which may be individually or collectively referred to herein as a "patch," without limitation. The patch 500 comprises a housing 502, a base layer 504, and pockets 508 defined by the housing 502. The pockets 508 are configured to receive electrode hydrogel therein. The pockets 508 form expansion slots 510 to form a tiered hydrogel pocket. The expansion slots 510 provide additional volume that allows the hydrogel to expand towards the patch 500 and away from the body of the living subject. An adhesive layer 506 is provided to adhere the patch 500 to the body of the living subject. The tiered pocket 508 improves mechanical adhesion to the skin of the living subject.

Figure 26:
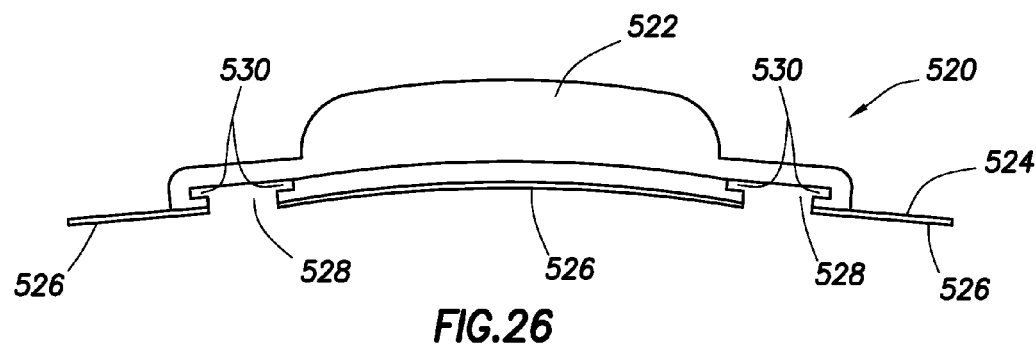
FIG. 26 is a side sectional view of one aspect of a form fitting preformed body associated device.

FIG. 26 is a side sectional view of one aspect of a form fitting preformed body associated device 520. In various aspects the body associated device 520 may be implemented as a patch, a biocollection patch, a patch receiver, a wearable personal communication device ("personal communicator"), among others, which may be individually or collectively referred to herein as a "patch," without limitation. The patch 520 comprises a preformed housing 522, a base layer 524, and tiered pockets 528 defined by the housing 520. The preformed housing 522 comprises a preformed body form factor with a curvature to conform to the contours of the body of the living subject to enhance better fitment to the body of the living subject. The tiered pockets 528 are configured to receive electrode hydrogel therein. The tiered pockets 528 form expansion slots 530 to form the tiered hydrogel pocket. As discussed above, the hydrogel is the interface between the metal flexible electrode circuits 136a-c (FIGS. 17-18). As the hydrogel expands, the patch has a tendency to be pushed away from the skin of the living subject and reduce electrical contact with the skin. Accordingly, the expansion slots 530 provide additional volume that allows the hydrogel to expand towards the patch 520 and away from the body of the living subject. This has a tendency to reduce the pull-away of the patch from the skin as the hydrogel expands. An adhesive layer 526 is provided to adhere the patch 520 to the body of the living subject. The tiered pocket 528 improves mechanical adhesion to the skin of the living subject.

Figure 27:
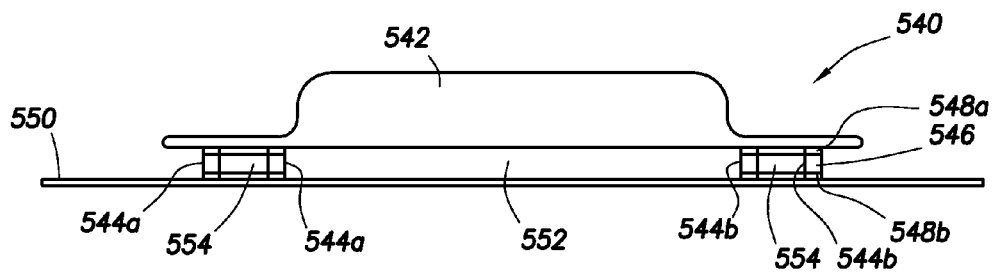
FIG. 27 is a side sectional view of one aspect of a body associated device.
Figure 28A:
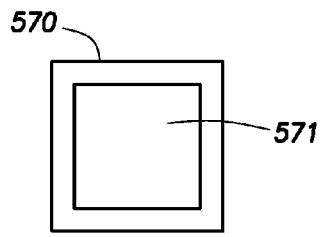
Figure 28B:
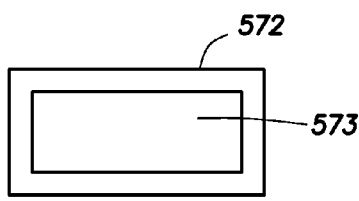
Figure 28C:
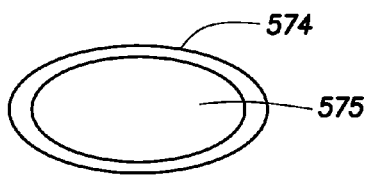
Figure 28D:
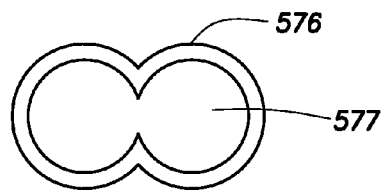

FIG. 27 is a side sectional view of one aspect of a body associated device 540. In various aspects the body associated device 540 may be implemented as a patch, a biocollection patch, a patch receiver, a wearable personal communication device ("personal communicator"), among others, which may be individually or collectively referred to herein as a "patch," without limitation. The patch 540 comprises a housing 542, standoffs 544a and 544b, (544a-b), and a base layer 550, where the base layer 550 is the adhesive layer that adheres to the skin of the living subject. In various aspects, the standoffs 544a-b comprise a flexible inner layer 546 and one or two adhesive outer layers 548a and/or 548b. In one aspect, the flexible inner layer 546 is formed from foam. The standoffs 544a-b are interposed between the patch housing 542 and the base layer 550. The standoffs 544a-b are attached to the housing by a first adhesive layer 548a and, in one aspect, are attached to the base layer 550 by a second adhesive layer 548b. The housing 542 and the base layer 550 define an airgap 552. Hydrogel 554 is located in the space defined by the standoffs 544a-b to form a hydrogel interface to the skin of the living subject. In various aspects, the number of attachments points can be anywhere from 1 to 10 or many more than 10. In various aspects, the standoffs 544a-b may be formed in the shape of a continuous circular ring as shown in FIG. 12, or a broken ring. Additionally, the standoffs 544a-b may be formed in any of the shapes described hereinbelow with reference to FIGS. 28A-D and 29A-D. As previously discussed, the attachment points between the patch 540 and the skin of the living subject may be determined by the shape of the standoffs 544, for example, as shown in FIGS. 12, 28A-D, and 29A-D. 5.

FIGS. 28A-D illustrate various standoffs having different continuous forms. Accordingly, in such aspects, in addition to the circular ring shape of the standoffs 114a-c shown in FIG. 12, the standoffs may be formed in any suitable shape such as a square shaped standoff 570, a rectangle shaped standoff 572, an oval shaped standoff 574, a kidney shaped standoff 576, where each of the shapes includes a continuous solid outer portion that defines an inner aperture or space. An electrode hydrogel may be located in the inner aperture 571, 573, 575, 577 defined by the corresponding standoffs 570, 572, 574, 576.

FIGS. 28A-D illustrate various standoffs having different continuous forms. Accordingly, in such aspects, in addition to the circular ring shape of the standoffs 114a-c shown in FIG. 12, the standoffs may be formed in any suitable shape such as a square shaped standoff 570, a rectangle shaped standoff 572, an oval shaped standoff 574, a kidney shaped standoff 576, where each of the shapes includes a continuous solid outer portion that defines an inner aperture or space. An electrode hydrogel may be located in the inner aperture 571, 573, 575, 577 defined by the corresponding standoffs 570, 572, 574, 576.

FIGS. 29A-D illustrate various standoffs having different broken forms. As shown in FIGS. 29A-D, for example, the broken standoff has a broken outer portion with an open portion in the form of a "C" for a broken square shaped standoff 580, a broken rectangle shaped standoff 582, and a broken oval shaped standoff 584, and in the form of an "E" for a broken kidney shaped standoff 586 shape. Although not shown, in one aspect, the circular ring shaped standoffs 114a-c (FIG. 12) can be formed in a broken "C" shape. An electrode hydrogel may be located in the inner aperture 581, 583, 585, 587 defined by the corresponding standoffs 580, 582, 584, 586.

FIG. 30 illustrates one aspect of a personal communication system 600 in which the body associated device described herein may be employed. As illustrated in FIG. 30, a body associated device 604 is positioned on a living subject 602. The body associated device 604 may be configured as any of the body associated devices 100, 200, 300, 320, 400, 420, 500, 520, 540 described above in connection with FIGS. 1-27 with any of the standoff shapes described with reference to FIGS. 12, 28A-D, 29A-D. The living subject 602 may be a human or a non-human being. In various aspects, the body associated device 604 may be realized in many forms and configurations as described above in connection with FIGS. 1-27. In addition, the body associated device 604 may be formed as sensor-enabled patches, watches, and jewelry, bandages with an adhesive portion, wristbands, earrings, bracelets, rings, pendants, clothing, undergarments, hats, caps, scarves, pins, accessories, belts, shoes, eyeglasses, contact lenses, hearing-aides, subcutaneous implants, and other devices that are wearable, implantable, or semi-implantable on or in the living subject 602 without limitation. The body associated device 604 is configured to communicate with the living subject 602 and an external local node 606. The external local node 606 is configured to communicate with a remote node 610 via a network 608. In one aspect, the body associated device 604 is configured to communicate with the remote node 610 directly. It will be appreciated that in the context of the present disclosure, communication is intended to encompass communications to and from the personal communicator 605 and the external local node 606. Likewise, communication is intended to encompass communications to and from the personal communicator 605 and the remote node 610 as well as communications to and from the external local node 606 and the remote node 610.

The body associated device 604 may comprise any number of distinct physiological parameter or biomarker collecting and/or sensing capabilities. The number of distinct parameters or biomarker collecting and/or sensing capabilities may vary e.g., one or more, two or more, three or more, four or more, five or more, ten or more, and so on. In certain configurations, the personal communicator 605 comprises one or more active components that are able to dynamically monitor and record individual physiological parameters and/or biomarkers associated with the living subject 602. Such components include, without limitation, sensors, electronic recording devices, processors, memory, communication components. In one aspect, the personal communicator 605 may include an on-board battery to supply electrical power to the active components. The physiological parameter or biomarker sensing abilities may include sensing cardio-data, including heart rate, electrocardiogram (ECG), and the like, respiration rate, temperature, pressure, chemical composition of fluid, e.g., analyte in blood, fluid state, blood flow rate, physical activity, sleep, accelerometer motion data, without limitation, for example.

In one aspect, the body associated device 604 provides specific information about the state of health of the subject 602. In another aspect, some of this information may be derived from sensors embedded in the body associated device 604. The subject 602 may obtain the body associated device 604 with a prescription, for example, and then wear the body associated device 604 for a prescribed period, e.g., hours, days, weeks, months, years.

In one aspect, the body associated device 604 includes, is configured to (a) monitor and record individual physiology, e.g., physical activity, heart rate, respiration, temperature, sleep, etc., of the living subject 602 and (b) communicate these parameters beyond the body of the living subject 602 to other devices, e.g., mobile phones, computers, internet servers, etc., in order to (c) enable support and collaboration for fitness, wellbeing, disease management, sport, entertainment, gaming, and other applications. A challenge for such body associated device 604 is creating a compelling rationale for the individual 602 to wear or use the personal communicator 605 on a continuous basis—for example, to apply an adhesive bandage-based body associated device 604, as described above in connection with FIGS. 1-26, to their skin for weeks, months and potentially years and accept the possibility of its inconveniences and limitations, such as (i) potential skin irritation, (ii) the burden of frequent application and removal, and (iii) a feeling of intrusiveness into the wearer's daily life.

In one aspect, the body associated device 604, for example a sensor patch that adheres to the skin of an individual such as the living subject 602, communicates with its wearer by sending and receiving tactile or other signals. The default settings may be modified such that the body associated device 604 discreetly vibrates or pulses in a specific manner or pattern, e.g., time or space based, to remind the subject 602 of important events or to communicate important personalized messages to the wearer. The default settings also may be modified such that the subject 602 can transmit and record meaningful inputs and messages to the body associated device 604 by communicating a simple language of finger taps, jiggles, scratches or other physical inputs initiated by the subject 602. In one aspect, the living subject 602 can communicate with the body associated device 604 through the pushbutton switch 108 (FIG. 1), which activates the switch 140 (FIG. 17). Through the body associated device 604 communications architecture, e.g., a Bluetooth or other communication links, to other devices beyond the body, the composite set of sensed physiology, tactile inputs, and outputs can be transmitted to other individuals, groups, caregivers, and related products, e.g., online games, of the subject's 602 choosing via the external local node 606, network 608, and/or the remote node 610. It will be appreciated that the term "communication architecture" is intended to cover any suitable communication architecture including, for example, body associated device 604 "patch" controls communications, other control communication device or devices, or any suitable permutation of a suitable communication control set. The features of the body associated device 604 are based on a sustained behavior change mechanism and it increases the value and potential of body associated device 604 and the likelihood that consumers will seek out, use, and benefit from such body associated device 604.

In-body communications include any communication of data or information via the body of the living subject 602, i.e., communication via or associated with inter-body aspects, intra-body aspects, and a combination of the same. For example, inter-body aspects include communications associated with devices designed to attach to a body surface. Intra-body aspects include communications associated with data generated from within the body, e.g., by the body itself or by a device implanted, ingested, or otherwise locatable in, or partially in, the body. For example, intra-body communications are disclosed in the PCT Patent Application No. PCT/US09/68128 dated Dec. 15, 2009, BODY-ASSOCIATED RECEIVER AND METHOD, the entire content of which is hereby incorporated by reference.

Communications include and/or may be associated with software, hardware, circuitry, various devices, and combinations thereof.

The devices include devices associated with physiologic data generation, transmission, reception, communication. The devices further include various implantable, ingestible, insertable, and/or attachable devices associated with the human body or other living organisms. As shown in FIG. 30, the body associated device 604 may be in communication with an IEM 612 and/or an implantable pulse generator 614 (IPG), e.g., pacer, etc., implanted near the heart region. The devices still further include multimedia devices such as telephones, stereos, audio players, PDAs, handheld devices, and multimedia players.

The system for incorporating physiologic data enables exchange, transmission, receipt, manipulation, management, storage, and other activities and events related to physiologic data. Such activities and events may be contained within the system for incorporating physiologic data, partially integrated with the system for incorporating physiologic data, or associated with externalities, e.g., activities, systems, components, and the like which are external to the system for incorporating physiologic data.

The physiologic data environment includes any source of information or data, including remote computer systems, local computer devices. The information or data may comprise physiologic data in whole or in part, e.g., aggregated or generated with other types of data. The physiologic data may be pure or refined, e.g., physiologic data from which inferences are drawn.

As shown in FIG. 30, the body associated device 604, regardless of form factor or implementation is in communication with an external local node 606. In one aspect, the personal communicator 605 includes the capability of communicating, e.g., receiving, transmitting, generating, and recording data directly or indirectly from the living subject 602. Although the data may include physiologic data, it is not limited as such. Any data of a physiologic nature may be associated with the living subject 602. The physiologic data may include, for example, heart rate, heart rate variability, respiration rate, body temperature, temperature of local environment, three-axis measurement of activity and torso angle, as well as other physiologic data, metrics, and indicators associated with one or more individuals. The physiologic data may be communicated at various times or time intervals to the external local node 606. For example, the communication may be real-time, i.e., in close temporal proximity to a time in which the physiologic data were generated, measured, ascertained, or on an historical basis, i.e., in far temporal proximity to a time in which the physiologic data was generated, measured, ascertained. In various aspects, the physiologic data may be associated with a variety of devices, e.g., cardiac device.

In one aspect, the external local node 606 may be configured as a communication hub and may include any hardware device, software, and/or communications component(s), as well as systems, subsystems, and combinations of the same which generally function to communicate physiologic and non-physiologic data between the body associated device 604 and the external local node 606. Communication of the data includes receiving, storing, manipulating, displaying, processing, and/or transmitting the data to the remote node 610 via the network 608.

In various aspects, the external local node 606 also functions to communicate, e.g., receive and transmit, non-physiologic data. Example of non-physiologic data include gaming rules and data generated by a separate cardiac-related device such as an implanted pacemaker and communicated to the hub directly or indirectly, e.g., via the body associated device 604.

Broad categories of external local nodes 606 include, for example, base stations, personal communication devices, handheld devices, and mobile telephones. In various aspects, the external local node 606 may be implemented as a handheld portable device, computer, mobile telephone, sometimes referred to as a smartphone, tablet personal computer (PC), kiosk, desktop computer, or laptop computer, or any combination thereof. Examples of smartphones include, for example, Palm® products such as Palm® Treo® smartphones, Blackberry® smart phones, Apple® iPhone® device, and the like. Although some aspects of the external local node 606 may be described with a mobile or fixed computing device implemented as a smart phone, personal digital assistant, laptop, desktop computer by way of example, it may be appreciated that the various aspects are not limited in this context. For example, a mobile computing device may comprise, or be implemented as, any type of wireless device, mobile station, or portable computing device with a self-contained power source, e.g., battery, such as the laptop computer, ultra-laptop computer, personal digital assistant (PDA), cellular telephone, combination cellular telephone/PDA, mobile unit, subscriber station, user terminal, portable computer, handheld computer, palmtop computer, wearable computer, media player, pager, messaging device, data communication device, and so forth. A fixed computing device, for example, may be implemented as a desk top computer, workstation, client/server computer, and so forth.

The external local node 606 comprises personal communication devices including, for example, devices having communication and computer functionality and typically intended for individual use, e.g., mobile computers, sometimes referred to as "handheld devices." Base stations comprise any device or appliance capable of receiving data such as physiologic data. Examples include computers, such as desktop computers and laptop computers, and intelligent devices/appliances. Intelligent devices/appliances include consumer and home devices and appliances that are capable of receipt of data such as physiologic data. Intelligent devices/appliances may also perform other data-related functions, e.g., transmit, display, store, and/or process data. Examples of intelligent devices/appliances include refrigerators, weight scales, toilets, televisions, door frame activity monitors, bedside monitors, bed scales. Such devices and appliances may include additional functionality such as sensing or monitoring various physiologic data, e.g., weight, heart rate. Mobile telephones include telephonic communication devices associated with various mobile technologies, e.g., cellular networks.

In various aspects, the external local node 606 may provide voice and/or data communications functionality in accordance with different types of cellular radiotelephone systems. Examples of cellular radiotelephone systems may include Code Division Multiple Access (CDMA) systems, Global System for Mobile Communications (GSM) systems, North American Digital Cellular (NADC) systems, Time Division Multiple Access (TDMA) systems, Extended-TDMA (E-TDMA) systems, Narrowband Advanced Mobile Phone Service (NAMPS) systems, 3G systems such as Wide-band CDMA (WCDMA), CDMA-2000, Universal Mobile Telephone System (UMTS) systems, WiMAX (Worldwide Interoperability for Microwave Access, LTE (Long Term Evolution) and so forth.

In various embodiments, the external local node 606 may be configured to provide voice and/or data communications functionality in accordance with different types of wireless network systems or protocols. Examples of suitable wireless network systems offering data communication services may include the Institute of Electrical and Electronics Engineers (IEEE) 802.xx series of protocols, such as the IEEE 802.1a/b/g/n series of standard protocols and variants (also referred to as "WiFi"), the IEEE 802.16 series of standard protocols and variants (also referred to as "WiMAX"), the IEEE 802.20 series of standard protocols and variants, and so forth. A mobile computing device may also utilize different types of shorter range wireless systems, such as a Bluetooth system operating in accordance with the Bluetooth Special Interest Group (SIG) series of protocols, including Bluetooth Specification versions v1.0, v1.1, v1.2, v1.0, v2.0 with Enhanced Data Rate (EDR), as well as one or more Bluetooth Profiles, and so forth. Other examples may include systems using infrared techniques or near-field communication techniques and protocols, such as electromagnetic induction (EMI) techniques.

In one aspect, the external local node 606, for example, the hub, includes a software application associated with a mobile telephone of a patient. The application and mobile telephone function to receive physiologic data from a receiver, which, in turn, receives the physiologic data directly from an individual or indirectly, e.g., via a device. Examples of devices include cardiac devices and ingestible devices. The hub stores, manipulates, and/or forwards the data, alone or in combination with other data, via the network 608 to a remote node 610.

In various aspects, the external local node 606 (hub) receives, generates, communicates, and/or transmits, physiologic data, alone or in combination with other data, i.e., non-physiologic data from various sources. Communication from the external local node 606 includes any transmission means or carriers, and combinations thereof, including wireless, wired, RF, conductive, etc. as is known in the art or as may become available in the future.

In various aspects, the handheld device includes software, e.g., a software agent/application, associated with the physiologic data. In various aspects of the handheld device, the software is preconfigured, i.e., configurable by the manufacturer/retailer; configurable by the consumer, i.e., downloadable from a website; or a combination of the same.

The base station includes systems, subsystems, devices, and/or components that receive, transmit, and/or relay the physiologic data. In various aspects, the base station communicably interoperates with a receiver such as the body associated device 604 and a communications network 608 such as the Internet. Examples of base stations are computers, e.g., servers, personal computers, desktop computers, laptop computers, intelligent devices/appliances, etc., as heretofore discussed.

In various aspects, the base station may be embodied as an integrated unit or as distributed components, e.g., a desktop computer and a mobile telephone in communication with one another and in communication with a patch receiver and the Internet.

In various aspects, the base station includes the functionality to wirelessly receive and/or wirelessly transmit data, e.g., physiologic data received from and transmitted to the body associated device 604 and the Internet.

Further, in various aspects, the base station may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

The mobile telephone includes, for example, devices such as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In addition to the standard voice function of a telephone, various aspects of mobile telephones may support many additional services and accessories such as short message service (SMS) for text messaging, email, packet switching for access to the Internet, java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

In various aspects, the mobile telephone includes software, e.g., a software agent/application, associated with the physiologic data. One example is an auto refill application related to or integrated with an auto refill system to facilitate automated prescription refill functions. In various aspects of the mobile telephone, the software is preconfigured, i.e., configurable by the manufacturer/retailer; configurable by the consumer, i.e., downloadable from a website; or a combination of the same.

Further, various aspects of the hub include combinations of devices. One such combination is the body associated device 604 in communication with the handheld device or the mobile telephone. Thus, for example, the body associated device 604 wirelessly transmits physiologic data to the mobile telephone having a receiver and a software agent available thereon. The receiver of the mobile telephone receives the physiologic data. A software agent, e.g., an application, processes the physiologic data and displays various information related to the physiologic data via, for example, a customized graphical user interface (GUI). In various aspects, the software agent generates displays with a predetermined "look and feel," i.e., recognizable to a user as belonging to a predetermined group of software programs, GUIs, source devices, communities, gaming software, etc.

More particularly, the personal communication system 600 includes any environment having therein, or associated with, data or communication of physiologic data for a gaming or recreational purpose. Communication includes any method, act, or vehicle of communication, and/or combinations thereof. For example, communication methods include manual, wired, and wireless. Wireless technologies include radio signals, such as x-rays, ultraviolet light, the visible spectrum, infrared, microwaves, and radio waves, etc. Wireless services include voice and messaging, handheld and other Internet-enabled devices, data networking.

Vehicles of communication include the network 608. In various aspects, the network 608 comprises local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

In one aspect, the remote node 610 comprises social network systems, commercial systems, healthcare systems, pharmacy systems, university systems, financial transaction systems, web communities, physician systems, family caregiver systems, regulatory agency systems, wholesaler/retailer systems as described in U.S. patent application Ser. No. 12/522,249 titled "INGESTIBLE EVENT MARKER DATA SYSTEM," the disclosure of which is herein incorporated by reference in its entirety. In other aspects, the remote node 110 comprises state games, behavioral reflective games, psychological response games, synchronization games, actual progress games, and recreational games as described in PCT Patent Application No. PCT/US09/60713 dated Oct. 14, 2009 titled "METHOD AND SYSTEM FOR INCORPORATING PHYSIOLOGIC DATA IN A GAMING ENVIRONMENT" and published as WO 2010/045385, the disclosure of which is herein incorporated by reference in its entirety.

In various aspects, the personal communication system 600 provides health monitoring, assessment, and sensing in a closed loop. Furthermore, the personal communication system 600 provides a framework for caregivers to communicate with patients and implement wellness and disease management programs. Using the body associated device 604 enables such communication to be conducted in a discreet manner. Servers at the remote node 610 may be configured as desired, e.g., to provide for subject directed permissions. For example, the servers may be configured to allow a family caregiver to participate in the subject's therapeutic regimen, e.g., via an interface (such as a web interface) that allows the family caregiver to monitor alerts and trends generated by the server, and provide support back to the subject 602. The servers also may be configured to provide responses directly to the subject, e.g., in the form of subject alerts, subject incentives, which are relayed to the subject via the communication device. The servers also may interact with a health care professional, e.g., RN, physician, which can use data processing algorithms to obtain measures of health and compliance of the subject, e.g., wellness index summaries, alerts, cross-patient benchmarks, and provide informed clinical communication and support back to the subject 602.

FIG. 31 is a block diagram of one aspect of a body associated device 604. The body associated device 604 may comprise features, in any suitable configuration and combination. In one aspect, the body associated device 604 comprises a power unit 702, an operation unit 704 that includes an electrode 704A, an operation or processing unit 706, and a memory unit 708. These and other electronic components are provided on the printed circuit board 128 (FIGS. 13-16). The body associated device 604 may include a power management module 710 that controls the power consumption. The body associated device 604 is configured to communicate with other near-by devices using one or more transmitters/receivers ("transceiver") module 712. As used herein, the term "transceiver" may be used in a very general sense to include a transmitter, a receiver, or a combination of both, without limitation. For example, the transceiver module 712 may be used for one-way or two-way communications with the external local node 606 and/or the remote node 610 (FIG. 30). Furthermore, the body associated device 604 may include various features such as an accelerometer 714 to detect the orientation of the body associated device 604. In instances where the subject 602 is laying down or in a horizontal position, the body associated device 604 is capable of detecting that position and the duration of time that the subject 602 remains in that position. In addition to detecting the orientation of the body associated device 604, in various aspects, the accelerometer 714 may be employed to detect other physical aspects of the body associated device 604 such as static or dynamic acceleration forces, proper acceleration, position, vibrations, and the like.

Additionally, the body associated device 604 may further include a personal monitoring portion comprising one or more sensors 716 to detect one or more distinct physiological parameters. By physiological parameter sensing ability is meant a capability of sensing a physiological parameter or biomarker, such as, but not limited to heart rate, respiration rate, temperature, pressure, chemical composition of fluid, e.g., analyte detection in blood, fluid state, blood flow rate, accelerometer motion data, IEGM (intra cardiac electrogram) data.

Accordingly, the body associated device 604 may include physiological parameter measuring tools that allows it to determine if the subject is simply laying down or if the subject has suffered some medical condition that has caused them to end-up in that position. For example, the subject may have had a heart attack and the body associated device 604 can detect that condition and in conjunction with information from the accelerometer 714, the body associated device 604 is able to determine that the subject has a potentially serious medical condition. Another example includes the instance where the subject suffers from an epileptic seizure. The accelerometer 714 provides information to the body associated device 604 and the information from the accelerometer 714 combined with the measured physiological parameters allows the body associated device 604 to determine that a medical condition is taking place or has taken place that will require immediate attention.

In accordance with the teaching of the present disclosure, the signal receiver aspects of the body associated device 604 may be configured to receive a conductive communication. The conductive communication may be associated with any physiologic part of the body or from a device that conductively transmits through a body using ionic emission through controlled release of mass from solid into a conducting solution or fluid. The communication may be produced by an ionic emission module or an IEM or a smart-parenteral delivery system. Ingestible event markers of interest include those described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; and PCT Application Serial No. PCT/US2008/077753 published as WO 2009/042812; the disclosures of which applications are herein incorporated by reference. Smart parenteral delivery systems are described in PCT Application Serial No. PCT/US2007/015547 published as WO 2008/008281; each of the foregoing disclosures is herein incorporated by reference in its entirety.

As the body associated device 604 of these aspects is configured to receive data encoded in current flow through a conductive fluid, the receiver and the device that emits the communication, e.g., a current signature, (such as an ingestible event marker 612 (IEM), FIG. 30) use the living body with which they are associated as a communication medium. To employ the body as a communication medium for the signal, the body fluids act as the conducting fluid and the body of the subject is used as a conduction medium for communication. As such, the communication that is transferred between devices, e.g., transferred from an ionic emission device, an RFID device, and/or other signal-emitting devices, to a receiver, e.g., the body associated device 604, travels through the body of the subject 602 (FIG. 30). The conductive communication of interest may be provided through and received from the skin and other body tissues of the body of the subject 602 in the form of electrical alternating current (a.c.) signals that are conducted through the body tissues. As a result, such signal receivers do not require any additional cable or hard wire connection between the device generating the communication and the device receiving the communication.

The body associated device 604 may include a transbody conductive communication module configured to receive a conductive communication. The transbody conductive communication module is a functional module that is configured to receive a conductive communication, such as a communication emitted by the IEM 612 (FIG. 30). Where desired, the transbody conductive communication module may be implemented by a high power functional block, such as described above. In some instances, the transbody conductive communication module is configured to receive an encoded communication, by which is meant that the communication has been modulated in some manner, e.g., using a protocol such as binary phase shift keying (BPSK), frequency shift keying (FSK), amplitude shift keying (ASK), etc. In such instances, the body associated device 604 transbody conductive communication module is configured to decode a received encoded communication emitted by an IEM. The body associated device 604 may be configured to decode the encoded communication in a low signal to noise ratio (SNR) environment, e.g., where there may be substantial noise in addition to the information of interest, e.g., an environment having an SNR of 7.7 dB or less. The personal communicator 605 may be further configured to decode the encoded signal with substantially no error. In certain aspects, the body associated device 604 has a high coding gain, e.g., a coding gain ranging from 6 dB to 12 dB, such as a coding gain ranging from 8 dB to 10 dB, including a coding gain of 9 dB. The body associated device 604 in accordance with various aspects can decode encoded communications with substantially no error, e.g., with 10% error or less.

In one aspect, the body associated device 604 comprises a feedback module 718. The feedback module 718 may be implemented with software, hardware, circuitry, various devices, and combinations thereof. The function of the feedback module 718 is to provide communication with the living subject 602 (FIG. 30) in a discreet, tactful, circumspect manner. Accordingly, in various aspects the feedback module 718 may be implemented to communicate with the subject 602 using techniques that employ visual, audio, vibratory/tactile, olfactory, and taste. Such techniques are non-detectable by other living subjects such as humans, for example. In one aspect, the feedback module 718 enables close, intimate, and non-verbal communication between the subject 602 and the body associated device 604. With the feedback module 718, the subject 602 can develop a unique language/vocabulary for communicating with the body associated device 604.

In one aspect, the feedback module 718 may employ visual communication techniques using light sources to enable communication between the subject 602 (FIG. 30) and the body associated device 604. In various aspects, light from light emitting diode (LED) sources, for example, may be optically channeled to the eye of the subject 602 through optical waveguides, fiber optics, reflection, refraction, total internal reflection, or other optical techniques for manipulating a beam of light or pulses of light to maintain discreet communication between the subject 602 and the body associated device 604. In other aspects, such discreet optical communication may be implemented by way of implanted LEDs into the structure of eyeglasses, contact lenses, or other wearable devices, in such as manner as to be detectable only by the subject 602. In other aspects, mirrors or lens arrangements may be configured to transmit discreet light pulses such that they are visible only by the subject 602. In other aspects, liquid crystal displays (LCD) may be integrated into contact lenses or eyeglasses to provide a discreet form of visual communication between the subject 602 and the body associated device 604. In other aspects, infrared (IR) techniques may be employed for discreet communication purposes.

In another aspect, the feedback module 718 may employ audio communication techniques to enable communication between the subject 602 (FIG. 30) and the body associated device 604. In one aspect, the subject 602 may wear a small speaker in the form of an ear piece, for example, such that the communication remains private between the subject 602 and the body associated device 604. In other aspects, the subject 602 may wear a form or hearing aid tuned to a particular frequency such that only the subject 602 is able to discern such audio communications. In either of the above described aspects, the audio communication may be transmitted by wire or wireless communication techniques. The audio communication may be implemented in the form of text-to-speech or in the form of audible "beeps" of varying pitch to represent a perceived fundamental frequency of a sound to enable the subject 602 to develop a customized dictionary. Other auditory attributes of musical tones along with duration, loudness, timbre, and sound source location may be employed to develop the dictionary. It will be appreciated that pitch may be compared in terms of "higher" and "lower" in the sense that allows the construction of melodies. Pitch may be quantified as a frequency in cycles per second (Hz). Furthermore, other psychoacoustical attributes of sound may be employed to carry out communications discreetly between the subject 602 and the body associated device 604. In other aspects, small microphones may be employed to detect speech and convert it into an electrical signal.

In another aspect, the feedback module 718 may employ vibratory/tactile communication techniques to enable communication between the subject 602 (FIG. 30) and the body associated device 604. In one aspect, the body associated device 604 may employ a piezoelectric element or eccentric wheel (or weights) to generate vibrations that are detectable only by the subject 602. Thus, in one aspect, the subject 602 may tap the body associated device 604 to communicate information therewith. Piezoelectric sensors may be used to receive taps from the subject 602 and convert the taps into electrical impulse that can be used to communicate between the subject 602 and the body associated device 604. Piezoelectric films such as piezoelectric fluoropolymer (PVDF) film or KYNAR®/PVDF piezoelectric film and other such films may be employed as, or part of, pyroelectric sensors, accelerometers, touch-sensitive sensors, contact microphones, pickups, or drum triggers among other devices.

In other aspects, microelectromechanical systems (MEMS) (also written as micro-electro-mechanical, Micro ElectroMechanical or microelectronic and microelectromechanical systems), which employ technology of very small mechanical devices driven by electricity may be employed to generate tactile impulses that are perceptible only by the subject 602 (FIG. 30). MEMS devices may be formed on very small scales and thus components between 1 to 100 micrometers in size (i.e., 0.001 to 0.1 mm) may be realized. MEMS devices generally range in size from 20 micrometers (20 millionths of a meter) to a millimeter and consist of a central unit that processes data, the microprocessor and several components that interact with the outside such as microsensors. MEMS may be fabricated using modified semiconductor device fabrication technologies, normally used to make electronics. These include molding and plating, wet etching (KOH, TMAH) and dry etching (RIE and DRIE), electro discharge machining (EDM), and other technologies capable of manufacturing small devices. An early example of a MEMS device is the resonistor—an electromechanical monolithic resonator.

Other aspects of tactile communication techniques include nerve or muscle stimulation techniques employing electrical impulses. For example, electrical current may be employed to stimulate muscle tissue. Electro-stimulation uses voltage in the range of about 0 to about 40 V and current in the range of about 0 to about 80 mA. Such low electrical energy levels are not harmful to the subject 602 and may be calibrated to optimize comfort versus sensitivity. For example, such voltages and currents are typical in transcutaneous electrical nerve stimulation (TENS), which currently is one of the most commonly used forms of electroanalgesia. In one aspect, trains of stimuli can be delivered with variable current strengths, pulse rates, and pulse widths as adjusted by the living subject 602. A preferred waveform is biphasic, to avoid the electrolytic and iontophoretic effects of a unidirectional current where typical stimulus parameters are amplitude, pulse width (duration), and pulse rate (frequency). In one aspect, the amplitude current may be set by the living subject 602 at a comfortable, low intensity level, just above threshold, pulse width may be set to anywhere in the range of about 10 to about 1000 microseconds, and the pulse rate may be set to anywhere in the range of about 80 to about 100 impulses per second (Hz); about 0.5 to about 10 Hz when the stimulus intensity is set high, for example. In one aspect, electrodes are placed in contact with the surface of the skin of the subject 602 to provide detectable stimulation. In other aspects, the electrodes may be embedded or partially embedded subcutaneously. In other aspects, galvanic skin response, electrical, electrostatic, or electromagnetic techniques may be employed to stimulate nerves or muscles to enable communication between the subject 602 and the body associated device 604.

Other aspects of tactile communication techniques include thermal stimulation techniques. For example, thermoelectric circuits may be employed on the body associated device 604 to generated sensations of hot and cold in varying degrees such that the subject 602 can develop a unique vocabulary based on thermally generated communications. A simple technique for generating thermal sensations includes driving a current through a resistor. More complex techniques exploit the thermoelectric effect where temperature differences are converted directly to electric voltage and vice versa. A thermoelectric device creates a voltage when there is a different temperature on each side. Conversely when a voltage is applied to it, it creates a temperature difference (known as the Peltier effect). At atomic scale (specifically, charge carriers), an applied temperature gradient causes charged carriers in the material, whether they are electrons or electron holes, to diffuse from the hot side to the cold side, similar to a classical gas that expands when heated; hence, the thermally induced current. The thermoelectric effect can be used to generate electricity, to measure temperature, to cool objects, or to heat them. Because the direction of heating and cooling is determined by the polarity of the applied voltage, thermoelectric devices make very convenient temperature controllers and thus can be used for communications between the subject 602 and the body associated device 604. Traditionally, the term thermoelectric effect or thermoelectricity encompasses three separately identified effects, the Seebeck effect, the Peltier effect, and the Thomson effect, any one of which may be employed to implement various aspects of tactile communication techniques.

In other aspects, tactile communication techniques include haptic sensors such as Electroactive Polymer Artificial Muscles (EPAM™) based on dielectric elastomers. Such sensors have the bandwidth and the energy density required to make haptic sensors that are responsive and compact. Such EPAM™ based dielectric elastomers may be configured into thin, high-fidelity haptic sensor modules to provide a brief tactile "click" that corresponds to a key press or tap.

In one aspect, the feedback module 718 may employ olfactory and taste communication techniques to enable communication between the subject 602 (FIG. 30) and the body associated device 604. A fluidic reservoir filled with an aromatic fluid may be used as a source for generating smells and tastes. In one aspect, an electrical current generated by the feedback module 718 may be driven through the fluidic reservoir to release the aromatic fluid. The sense of smell or taste may increase proportionately with the electrical current through the fluidic reservoir. Other techniques include solid state devices that outgas when an electrical current is passed therethrough and substrates with aromatic material embedded in wax that release aromas when an electrical current is passed therethrough. Such techniques may be configured for single use or multiuse. Although these techniques are suitable for communicating information from the body associated device 604 to the subject 602, the subject 602 may use any other techniques described herein to communicate information to the body associated device 604 such as tapping an external housing of the body associated device 604.

The body associated device 604 may incorporate various form factors and materials. In one example, the body associated device 604 may be in the form of a patch similar in design, shape, size, and material to an adhesive bandage, i.e., may be removably-attachable to the subject 602 (FIG. 30). Specific dynamics of design, shape, design, and material may vary according to use, environment, placement. For example, the design may incorporate various constructs and patterns. The constructs, for example, may include one or more layers, e.g., a substrate having an adhesive layer. The patterns may include various aesthetic features, e.g., various patterns, various colors, decals, imprints, etc., and non-aesthetic features, e.g., breathable materials, non-allergenic materials. The shape may vary, e.g., oval, circular, triangular, kidney-shaped, rectangular, square. The size may vary, e.g., approximately 75 mm by 120 mm, approximately 50 mm by 80 mm, approximately 25 mm by 40 mm, and with a thickness ranging from approximately 2 mm to approximately 20 mm, or other sizes, as desired. The material may incorporate any material or combinations of materials capable of carrying out the functionality of the body associated device 604 as herein described. Further, in various aspects, considerations may be given to position, energy conservation schemes, carrier identification, decoding and error correcting.

The processing unit 706 communicate with the sensors 716 and/or other devices. In various aspects, for example, the processing unit 706 generates electronic communication with the sensors 716. In one example, the processing unit 706 includes electronic integrated circuits (not shown). In various aspects, a housing may include various features, e.g., watertight, hermetically sealed. The circuit board having electronic circuits may electronically communicate with the sensors 716. The power unit 702 may, for example, be a rechargeable power source such as a rechargeable battery. The power unit in another aspect may be a passive device that receives power from an external source, e.g., passive RFID.

In various aspects, different energy conservation schemes may be considered. Such schemes include a periodic wake-up, e.g., sensors and/or other components wake-up periodically such that energy, e.g., power source unit 702, is conserved during non-awake periods. Such energy conservation schemes may be controlled by the power management module 710.

In various aspects, the body associated device 604 may accomplish one or more of sensing functions using a communication receiving element, e.g., using electrodes of the body associated device 604 for receiving communications and sensing applications, or the body associated device 604 may include one or more distinct sensing elements that are different from the signal receiving element. The number of distinct sensing elements that may be present on (or at least coupled to) the signal receiver may vary, and may be one or more, two or more, three or more, four or more, five or more, ten or more.

In various aspects, the body associated device 604 may include a pair of electrodes that provide for dual functions of receiving and sensing information or communications. For example, the electrodes also may serve additional sensing functions. In certain aspects, the electrodes may be used to generate an IEGM (intra cardiac electrogram) at whatever site they are located. From that data, there are many kinds of processing that can be done, e.g., to detect various cardiac events, such as tachycardia, fibrillations, heart rate. Another sensing capability that may be accomplished with two electrodes of the signal receiver employs measuring the impedance between the electrodes. The measured impedance will have some component which is determined by the trans-thoracic impedance, which relates to respiration. In this manner, the impedance data can be employed to obtain the respiratory rate of the subject. The electrodes may also be employed as sensors of fluid state of subject.

As mentioned above, one or more additional physiologic sensors distinct from the electrodes may be included in the body associated device 604. For example, a temperature sensor, e.g., a thermistor, may be included therein. If really precise temperature measurement are desired, there are other techniques like resistive temperature devices (RTDs), made out of platinum generally, which can give very precise measurements of temperature. An additional physiological sensor may include an LED and a photodiode combined into a pulse-oximeter, which may be employed to measure blood oxygenation, which also may provide information about pulse pressure.

In addition, the body associated device 604 may include a pressure sensor, e.g., where the body associated device 604 is implanted next to an artery to get measurements of arterial blood pressure. For example, one can get the pressure inside the body by putting a pressure sensitive membrane on the surface of the body associated device 604. To get a more useful type of pressure, one usually wants to measure the venous or arterial blood pressure. In such a case, the membrane may be located in proximity to either an artery or a vein, so that as the artery pulsed it may exert a pressure on the pressure sensor. That could be calibrated to give an absolute pressure reading. Another possibility includes some sort of outrigger cuff, e.g., which cuffed around the artery. It could have strain gauges in it to measure pressure deflections, which are then attached to the receiver, e.g., the body associated device 604.

Generally, the body associated device 604 may also include analyte detection sensors. For example, specific chemical sensors may be incorporated into the signal receivers to detect the presence of various agents, e.g., glucose, BNP (B-type Natriuretic, which is associated with cardiac disease). There are other ways that one could build an oxygen sensor, including selectively porous impedance cells, where the oxygen changes the pH of a cell, and then the conductivity of that is measured. Where the signal receiver includes an analyte detecting sensing element, this sensing element can be configured in the signal receiver in a number of different ways. For example, a sensor that includes a selectively permeable membrane which is permeable to the agent to be detected may be provided, where there is an isolated cell behind it, and the agent passes through the membrane, and changes the properties, usually electrical properties, of the cell, which are then measured. For example, there may be a small reservoir on the side of the signal receiver with a membrane across it, and the measuring electrical circuitry behind it. Another way of detecting agents employs sensors known in the art as ChemFET sensors, which are based on the binding of analyte to the sensor causing a change in the conductivity. There may be included a material with electrical properties (or other properties) that are changed when the material binds to it. Various proteins may be detected that way.

In one aspect, the body associated device 604 gathers physiologic data. The physiologic data includes data associated physiologic events, parameters, measurements. Such data include, for example, Galvanic skin response, heart rate, heart rate variability, respiration rate, body temperature, temperature of local environment, three-axis measurement of activity and torso angle, optical, pressure, sound, biochemical/biological, weight, position, derived electromyography (EMG), and electroencephalography (EEG). The physiologic data further include those data set out in the U.S. patent application Ser. Nos. 10/734,490; 10/764,429; 10/764,127; 10/764,125; 11/025,657; 11/324,196; 11/664,340; 11/731,786; 11/718,201; 11/897,942; 11/912,475; 12/063,097; 12/063,095; as well as PCT Application Serial Nos: PCT/US2007/015547; and PCT/US2008/52845, each of which is incorporated herein in its entirety by reference.

FIG. 32 is a block functional diagram of one aspect of an electronic circuit component of a body associated device 604. The electronic circuit component can be disposed on the printed circuit board 128 (FIG. 13-16) or may be formed on an integrated circuit component, which is then disposed on the printed circuit board 128 or a combination thereof. In FIG. 32, the body associated device 604 includes an electrode input 810. Electrically coupled to the electrode input 810 are a transbody conductive communication module 820 and a physiological sensing module 830. In one aspect, the transbody conductive communication module 820 is implemented as a first, e.g., high, frequency (HF) signal chain and the physiological sensing module 830 is implemented as a second, e.g., low, frequency (LF) signal chain. Also shown are CMOS temperature sensing module 840 (for detecting ambient temperature) and a 3-axis accelerometer 850. The body associated device 604 also includes a processing engine 860 (for example, a microcontroller and digital signal processor), a non-volatile memory 870 (for data storage), and a wireless communication module 880 (to receive data from and/or transmit data to another device, for example in a data download/upload action, respectively). In various aspects, the communication modules 820, 880 may comprise one or more transmitters/receivers ("transceiver") modules. As used herein, the term "transceiver" may be used in a very general sense to include a transmitter, a receiver, or a combination of both, without limitation.

The sensors 716 typically contact the subject's 602 (FIG. 30) person, e.g., are removably attached to the torso. In various aspects, the sensors 716 may be removably or permanently attached to the body associated device 604. For example, the sensors 716 may be removably connected to the body associated device 604 by snapping metal studs. The sensors 716 may comprise, for example, various devices capable of sensing or receiving the physiologic data. The types of sensors 716 include, for example, electrodes such as biocompatible electrodes. The sensors 716 may be configured, for example, as a pressure sensor, a motion sensor, an accelerometer, an electromyography (EMG) sensor, an ingestible event marker, a biopotential sensor, an electrocardiogram sensor, a temperature sensor, a tactile event marker sensor, and an impedance sensor.

The feedback module 718 may be implemented with software, hardware, circuitry, various devices, and combinations thereof. The function of the feedback module 718 is to provide communication with the living subject 602 (FIG. 30) in a discreet, tactful, circumspect manner as described above. In various aspects the feedback module 718 may be implemented to communicate with the subject 602 using techniques that employ visual, audio, vibratory/tactile, olfactory, and taste.

FIG. 33 illustrates one aspect of a body associated device 604 configured to be placed on an external topical location of a subject 602 (FIG. 30), such as a chest area. The body associated device 604 includes an upper housing plate 910 (such as may be fabricated from a suitable polymeric material), and includes indicator devices for example, a manually depressible operation button 902 in communication with a status identifier LED 903, which may be used to relay to an observer that the signal receiver is operating. Manually depressible operation button 902 can be manually manipulated to transition the signal receiver from a storage mode to a non-storage mode. Manually depressible operation button 902 can be manually manipulated to transition the signal receiver from a storage mode to a non-storage mode. When the signal receiver is in the storage mode, a micro-controller of the signal receiver may remain in a low duty cycle active state at all times to process input from the on/off button, and the digital signal processor (DSP) of the signal receiver powered off. When the on/off button is depressed to turn on the signal receiver, the micro-controller de-bounces the input and powers the DSP into its idle state. While in storage mode, the device may draw less than 10

μA, including 5 μA of current or less, such as 1 μA or less and including 0.1 μA or less. This configuration enables the device to remain at greater than 90% useful battery life if stored for one month (assuming the presence of a 250 mAH battery). Such a button may also be employed for other functions. For example, such a button may be employed to instruct the signal receiver to obtain certain types of data. In addition or alternatively, such a button may be employed to manually instruct the signal receiver to transfer data to another device. The various functional aspects of the feedback module 718 (FIGS. 31, 32) are incorporated into the body associated device 604 shown in FIG. 33 as may be dictated by a particular application.

Notwithstanding the claims, the invention is also referred to in the following clauses:

1. A device attachable to the body, comprising:
   a housing;
   an adhesive layer configured to be applied to a body of a living subject; and
   a standoff located between the housing and the adhesive layer.
2. The device of clause 1, wherein the housing and the adhesive layer define an airgap therebetween.
3. The device of clause 1 or 2, wherein the standoff is defined by any one of a continuous or broken ring, square, rectangular, oval, kidney shape and a predetermined thickness.
4. The device of clause 3, wherein the standoff defines at least one inner aperture configured to receive an electrode hydrogel therein.
5. The device of clause 4, further comprising an electrode hydrogel located in the inner aperture.
6. The body according to any of the preceding clauses wherein the standoff is formed of a foam material and/or wherein the standoff comprises a layer of adhesive formed on one end thereof.
7. The device according to any of the preceding clauses further comprising an attachment point between the housing and the adhesive layer, wherein an attachment area is defined by the shape of the standoff.
8. The device of clause 7, wherein the number of attachment points between the housing and the adhesive ranges from at least 1-10 or more.
9. The device according to any of the preceding clauses further comprising a flexible layer attached to the housing.
10. The device according to clause 9, wherein the housing and the flexible layer define an airgap therebetween.
11. The device of any of the clauses 9 or 10, wherein the flexible layer is made of foam.
12. The device of any of the clauses 9-11 wherein the flexible layer is interposed between the standoff and the housing.
13. The device according to any of the preceding clauses wherein the housing is formed of a flexible material.
14. The device according to any of the preceding clauses wherein the housing comprises a top portion and a bottom portion, and wherein the top and bottom portions define a slot therebetween, which slot enables the bottom portion to flex and adhere to a contour of the body of the living subject.
15. The device according to any of the preceding clauses wherein the housing comprises a curved preformed body form factor to enhance fitment to the body of the living subject.
16. The device according to any of the preceding clauses wherein the housing defines at least one pocket formed therein to receive electrode hydrogel.
17. The device according to any of the preceding clauses further comprising at least one tiered pocket configured to receive electrode hydrogel therein, wherein the tiered pocket forms an expansion slot.
18. The device according to any of the preceding clauses further comprising an electronic module located within the housing.
19. The device of clause 18, comprising at least one conductive element electrically coupled to the electronic module.
20. The device of clause 18 or 19 further comprising a transceiver electrically coupled to the electronic module.
21. The device according to any of the clauses 18-20 comprising a switch electrically coupled to the electronic module.
22. The device according to any of the clauses 18-21 further comprising a water ingress indicator electrically coupled to the electronic module.
23. The device according to any of the clauses 18-22 further comprising an energy source to power an indicator electrically coupled to the electronic module; wherein the indicator is located within the housing.
24. The device of clause 23, wherein a portion of the housing is formed of a translucent material to enable energy emitted by the indicator to be discernable to the living subject or detectable by electronic components external to the housing.
25. The device according to any of the clauses 18-24 wherein a hydrogel is electrically coupled to the circuit module.
26. The device according to any of the preceding clauses further comprising a physiological sensing module operative to sense physiological information from the subject.
27. A personal communication system, comprising a body associated device according to any of the preceding clauses designed to be worn by a living subject, the device further comprising a feedback portion coupled to the housing and to the electronic module, the feedback portion configured to communicate information between the living subject and the body associated device; and an external local node operative to transmit communications to and/or receive communications from the body associated device.
28. The personal communication system of clause 27 wherein the body associated device comprises a wireless communication module operative to communicate information from the device to the external local node and/or receive information from the external local node.
29. The personal communication system of any of the clauses 27-28 further comprising a remote node operative to communicate at least one of transmit communications to and receive communications from the external local node.
30. Use of a device according to any of the preceding clauses 1-26 for communicating information, preferably physiological parameters from a subject wearing the device, and/or for receiving information.
31. Device according to any of the preceding clauses 1-26 having the form of a patch.

It is to be understood that this disclosure is not limited to particular embodiments or aspects described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as solely, only and the like in connection with the recitation of claim elements, or use of a negative limitation.

As will be apparent to those of skill in the art upon reading this disclosure, each of the individual embodiments described and illustrated herein has discreet components and features which may be readily separated from or combined with the features of any of the other several embodiments without departing from the scope or spirit of the present invention. Any recited method can be carried out in the order of events recited or in any other order which is logically possible.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the scope of the appended claims.

Accordingly, it will be appreciated that those skilled in the art will be able to devise various arrangements which, although not explicitly described or shown herein, embody the principles of the invention and are included within its scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary aspects and embodiments shown and described herein. Rather, the scope of present disclosure is embodied by the appended claims.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "attached," "coupled," and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. In another example, some aspects may be described using the term "attached" to indicate that two or more elements are in direct physical contact. The term "attached," however, also may mean that two or more elements are not in direct contact with each other, but yet still co-operate or interact with each other.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

The invention claimed is:

1. A body associated device, comprising:
   a housing;
   an adhesive layer configured to be applied to a body of a living subject;
   at least two standoffs located between the housing and the adhesive layer and comprising at least two attachment points between the housing and the adhesive, wherein an attachment area is defined by the shape of the at least two standoffs, wherein the at least two standoffs define a uniform height;
   an electronic module located within the housing and comprising at least one electrode and a transceiver coupled to an antenna, wherein the transceiver and antenna enable wireless communication between the electronic module and local/remote nodes external to the body of the living subject; and
   wherein the wireless communication is communication associated with data generated from a first device within the body; and
   wherein the electronic module is configured to receive a conductive communication from the first device within the body via the at least one electrode; and
   wherein one of the at least two standoffs defines at least one inner aperture configured to receive an electrode hydrogel therein; and wherein the electrode hydrogel is located in the at least one inner aperture defined by the one of the at least two standoffs, wherein the electrode hydrogel is electrically coupled to the electronic module, and wherein the at least one electrode is coupled to the body via the electrode hydrogel located in the at least one inner aperture defined by the one of the at least two standoffs.

2. The body associated device of claim 1, wherein the number of attachment points between the housing and the adhesive ranges from 2 to 10.

3. The body associated device of claim 1, wherein the number of attachment points between the housing and the adhesive is greater than 10.

4. The body associated device of claim 1, wherein the conductive communication comprises data encoded in a current flow.

5. A body associated device, comprising:
a housing formed of a flexible material;
an adhesive layer configured to be applied to a body of a living subject;
at least two standoffs located between the housing and the adhesive layer, wherein the at least two standoffs define a uniform height;
an electronic module located within the housing and comprising at least one electrode and a transceiver coupled to an antenna, wherein the transceiver and antenna enable wireless communication between the electronic module and local/remote nodes external to the body of the living subject; and
wherein the wireless communication is communication associated with data generated from a first device within the body; and
wherein the electronic module is configured to receive a conductive communication from the first device within the body via the at least one electrode;
wherein one of the at least two standoffs defines at least one inner aperture configured to receive an electrode hydrogel therein; and
wherein the electrode hydrogel is located in the at least one inner aperture defined by the one of the at least two standoffs, wherein the electrode hydrogel is electrically coupled to the electronic module, and wherein the at least one electrode is coupled to the body via the electrode hydrogel located in the at least one inner aperture defined by the one of the at least two standoffs.

6. The body associated device of claim 5, wherein the housing comprises a top portion and a bottom portion, and wherein the top and bottom portions define at least one slot therebetween, the at least one slot enabling the bottom portion to flex and adhere to a contour of the body of the living subject.

7. The body associated device of claim 5, wherein the housing comprises a curved preformed body form factor to enhance better fitment to the body of the living subject.

8. The body associated device of claim 5, wherein the at least one inner aperture comprises at least one tiered pocket configured to receive electrode hydrogel therein, wherein the tiered pocket forms an expansion slot.

9. A body associated device, comprising:
a housing;
an adhesive layer configured to be applied to a body of a living subject;
at least two standoffs located between the housing and the adhesive layer, wherein the at least two standoffs define a uniform height; and
an electronic module located within the housing and comprising at least one electrode and a transceiver coupled to an antenna, wherein the transceiver and antenna enable wireless communication between the electronic module and local/remote nodes external to the body of the living subject; and
wherein the wireless communication is communication associated with data generated from a first device within the body; and
wherein the electronic module is configured to receive a conductive communication from the first device within the body via the at least one electrode; and
wherein one of the at least two standoffs defines at least one inner aperture configured to receive an electrode hydrogel therein; and
wherein the electrode hydrogel is located in the at least one inner aperture defined by the one of the at least two standoffs, wherein the electrode hydrogel is electrically coupled to the electronic module, and wherein the at least one electrode is coupled to the body via the electrode hydrogel located in the at least one inner aperture defined by the one of the at least two standoffs.

10. The body associated device of claim 9, further comprising a switch electrically coupled to the electronic module.

11. The body associated device of claim 9, further comprising a water ingress indicator electrically coupled to the electronic module.

12. The body associated device of claim 9, further comprising an indicator and an energy source capable of powering the indicator electrically coupled to the electronic module, wherein the indicator is located within the housing.

13. The body associated device of claim 12, wherein at least a portion of the housing is formed of a translucent material to enable energy emitted by the indicator to be discernable to the living subject or detectable by electronic components external to the housing.

14. The body associated device of claim 9, wherein at least one of the at least two standoffs is defined by any one of a continuous or broken ring, square, rectangular, oval, or kidney shape and a predetermined thickness.

15. A personal communication system, comprising:
a body associated device to be worn by a living subject, comprising:
a housing;
an adhesive layer configured to be applied to a body of the living subject;
at least two standoffs located between the housing and the adhesive layer, wherein the at least two standoffs define an air gap between the housing and the adhesive layer, wherein the at least two standoffs define a uniform height;
an electronic module located within the housing, wherein the electronic module comprises at least one electrode and a transceiver coupled to an antenna;
a feedback portion coupled to the housing and to the electronic module, the feedback portion configured to communicate information between the living subject and the body associated device; and
an external local node operative to provide at least one of transmitting communications to or receiving communications from the body associated device, wherein the communications are associated with data generated from a first device within the body, and wherein the transceiver and antenna enable wireless communication between the electronic module and the external local node external to the body of the living subject; and wherein the electronic module is configured to receive a conductive communication from the first device within the body via the at least one electrode;

wherein one of the at least two standoffs is defined by any one of a continuous or broken ring, square, rectangular, oval, or kidney shape and a predetermined thickness, wherein the one of the at least two standoffs defines at least one inner aperture configured to receive an electrode hydrogel therein; and wherein the electrode hydrogel is located in the at least one inner aperture defined by the one of the at least two standoffs, wherein the electrode hydrogel is electrically coupled to the electronic module, and wherein the at least one electrode is coupled to the body via the electrode hydrogel located in the at least one inner aperture defined by the one of the at least two standoffs.

16. The personal communication system of claim 15, wherein the body associated device further comprises:

a physiological sensing module operative to sense physiological information from the living subject.

17. The personal communication system of claim 15, further comprising:

a remote node operative to provide at least one of transmitting communications to or receiving communications from the external local node.

* * * * *